(12) United States Patent
Kaplan et al.

(10) Patent No.: US 9,724,105 B2
(45) Date of Patent: *Aug. 8, 2017

(54) METHODS AND APPARATUS FOR TRANSPERICARDIAL LEFT ATRIAL APPENDAGE CLOSURE

(71) Applicant: SentreHEART, Inc., Redwood City, CA (US)

(72) Inventors: Aaron V. Kaplan, Los Altos, CA (US); Jordan T. Bajor, Palo Alto, CA (US)

(73) Assignee: SentreHEART, Inc., Redwood City, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 14/604,632

(22) Filed: Jan. 23, 2015

(65) Prior Publication Data
US 2015/0157330 A1    Jun. 11, 2015

Related U.S. Application Data

(60) Continuation of application No. 11/944,522, filed on Nov. 23, 2007, now Pat. No. 8,974,473, which is a
(Continued)

(51) Int. Cl.
*A61B 17/128*    (2006.01)
*A61B 17/12*    (2006.01)
(Continued)

(52) U.S. Cl.
CPC .......... *A61B 17/1285* (2013.01); *A61B 17/12* (2013.01); *A61B 17/12013* (2013.01);
(Continued)

(58) Field of Classification Search
CPC ................ A61B 17/1285; A61B 17/12; A61B 17/12013; A61B 2017/320048; A61B 2017/00243; A61B 17/10; A61B 17/122
See application file for complete search history.

(56) References Cited

U.S. PATENT DOCUMENTS 1,376,754 A    5/1921    Fulton
1,468,599 A    9/1923    Longino
(Continued)

FOREIGN PATENT DOCUMENTS

CN    101262823 B    12/2011
EP    0 317 490 A2    5/1989
(Continued)

OTHER PUBLICATIONS

Advisory Action mailed on Jan. 31, 2005, for U.S. Appl. No. 10/007,364, filed Nov. 5, 2011, 3 pages.
(Continued)

*Primary Examiner* — Julian W Woo
(74) *Attorney, Agent, or Firm* — Cooley LLP

(57) ABSTRACT

Methods for closing a left atrial appendage rely on introducing a closure tool from a location beneath the rib cage, over an epicardial surface, and to the exterior of the left atrial appendage. The closure device may then be used to close the left atrial appendage, preferably at its base, by any one of a variety of techniques. One specific technique uses graspers and a closing loop. Methods may include advancing a closure tool adjacent to the left atrial appendage using a sub-xiphoid approach and closing the left atrial appendage using the closure tool. Methods may also include advancing a loop adjacent to the left atrial appendage using a sub-xiphoid approach and closing the left atrial appendage using the loop.

20 Claims, 13 Drawing Sheets

Related U.S. Application Data continuation of application No. 10/105,978, filed on Mar. 25, 2002, now Pat. No. 7,318,829, which is a division of application No. 10/007,364, filed on Nov. 5, 2001, now Pat. No. 7,226,458, which is a division of application No. 09/315,601, filed on May 20, 1999, now Pat. No. 6,488,689.

(51) Int. Cl.
    *A61B 17/10*     (2006.01)
    *A61B 17/122*     (2006.01)
    *A61B 17/00*     (2006.01)
    *A61B 17/32*     (2006.01)

(52) U.S. Cl.
    CPC ............ *A61B 17/10* (2013.01); *A61B 17/122* (2013.01); *A61B 2017/00243* (2013.01); *A61B 2017/320048* (2013.01)

(56) References Cited

U.S. PATENT DOCUMENTS

| | | |
|---|---|---|
| 2,131,321 A | 9/1938 | Hart |
| 3,496,932 A | 2/1970 | Prisk et al. |
| 3,677,597 A | 7/1972 | Stipek |
| 3,703,169 A | 11/1972 | Ouchi |
| 3,802,074 A | 4/1974 | Hoppe |
| 3,820,544 A | 6/1974 | Semm |
| 3,841,685 A | 10/1974 | Kolodziej |
| 3,871,379 A | 3/1975 | Clarke |
| 3,896,793 A | 7/1975 | Mitsui et al. |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,190,042 A | 2/1980 | Sinnreich |
| 4,217,891 A | 8/1980 | Carson |
| 4,249,536 A | 2/1981 | Vega |
| 4,257,278 A | 3/1981 | Papadofrangakis et al. |
| 4,280,510 A | 7/1981 | O'Neill |
| 4,319,562 A | 3/1982 | Crosby |
| 4,369,768 A | 1/1983 | Vukovic |
| 4,579,348 A | 4/1986 | Jones |
| 4,596,530 A | 6/1986 | McGlinn |
| 4,662,377 A | 5/1987 | Heilman et al. |
| 4,706,655 A | 11/1987 | Krauter |
| 4,744,363 A | 5/1988 | Hasson |
| 4,759,348 A | 7/1988 | Cawood |
| 4,765,341 A | 8/1988 | Mower et al. |
| 4,798,593 A | 1/1989 | Iwatschenko |
| 4,817,608 A | 4/1989 | Shapland et al. |
| 4,841,949 A | 6/1989 | Shimizu et al. |
| 4,865,037 A | 9/1989 | Chin et al. |
| 4,901,405 A | 2/1990 | Grover et al. |
| 4,909,789 A | 3/1990 | Taguchi et al. |
| 4,934,340 A | 6/1990 | Ebling et al. |
| 4,935,027 A | 6/1990 | Yoon |
| 4,944,753 A | 7/1990 | Burgess et al. |
| 4,991,578 A | 2/1991 | Cohen et al. |
| 4,991,603 A | 2/1991 | Cohen et al. |
| 4,998,975 A | 3/1991 | Cohen et al. |
| 5,033,477 A | 7/1991 | Chin et al. |
| 5,071,428 A | 12/1991 | Chin et al. |
| 5,108,406 A | 4/1992 | Lee |
| 5,144,942 A | 9/1992 | Decarie et al. |
| 5,163,942 A | 11/1992 | Rydell |
| 5,163,946 A | 11/1992 | Li |
| 5,163,949 A | 11/1992 | Bonutti |
| 5,176,691 A | 1/1993 | Pierce |
| 5,181,123 A | 1/1993 | Swank |
| 5,181,919 A | 1/1993 | Bergman et al. |
| 5,226,535 A | 7/1993 | Roshdy et al. |
| 5,226,908 A | 7/1993 | Yoon |
| 5,230,705 A | 7/1993 | Wilk |
| 5,234,455 A | 8/1993 | Mulhollan |
| 5,242,459 A | 9/1993 | Buelna |
| 5,243,977 A | 9/1993 | Trabucco et al. |
| 5,250,054 A | 10/1993 | Li |
| 5,267,968 A | 12/1993 | Russo |
| 5,267,970 A | 12/1993 | Chin et al. |
| 5,269,326 A | 12/1993 | Verrier |
| 5,281,238 A | 1/1994 | Chin et al. |
| 5,300,078 A | 4/1994 | Buelna |
| 5,306,234 A | 4/1994 | Johnson |
| 5,318,527 A | 6/1994 | Hyde et al. |
| 5,318,578 A | 6/1994 | Hasson |
| 5,336,229 A | 8/1994 | Noda |
| 5,336,231 A | 8/1994 | Adair |
| 5,336,252 A | 8/1994 | Cohen |
| 5,361,895 A | 11/1994 | Wilson et al. |
| 5,366,446 A | 11/1994 | Tal et al. |
| 5,373,840 A | 12/1994 | Knighton |
| 5,382,238 A | 1/1995 | Abrahamson et al. |
| 5,385,156 A | 1/1995 | Oliva |
| 5,387,219 A | 2/1995 | Rappe |
| 5,398,944 A | 3/1995 | D'Alfonso et al. |
| 5,403,331 A | 4/1995 | Chesterfield et al. |
| 5,405,351 A | 4/1995 | Kinet et al. |
| 5,417,684 A | 5/1995 | Jackson et al. |
| 5,417,697 A | 5/1995 | Wilk et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,367 A | 9/1995 | Kadry |
| 5,494,240 A | 2/1996 | Waugh |
| 5,498,228 A | 3/1996 | Royalty et al. |
| 5,520,701 A | 5/1996 | Lerch |
| 5,540,711 A | 7/1996 | Kieturakis et al. |
| 5,545,138 A | 8/1996 | Fugosa et al. |
| 5,545,178 A | 8/1996 | Kensey et al. |
| 5,569,290 A | 10/1996 | McAfee |
| 5,571,161 A | 11/1996 | Starksen |
| 5,582,580 A | 12/1996 | Buckman, Jr. et al. |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,653,716 A | 8/1997 | Malo et al. |
| 5,656,012 A | 8/1997 | Sienkiewicz |
| 5,676,162 A | 10/1997 | Larson, Jr. et al. |
| 5,676,636 A * | 10/1997 | Chin ............... A61B 17/0218 600/209 |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,725,521 A | 3/1998 | Mueller |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,189 A | 6/1998 | Matsuno |
| 5,766,216 A | 6/1998 | Gangal et al. |
| 5,766,217 A | 6/1998 | Christy |
| 5,766,687 A | 6/1998 | Rappoport |
| 5,769,848 A | 6/1998 | Wattanasirichaigoon |

(56) References Cited

U.S. PATENT DOCUMENTS

| | | |
|---|---|---|
| 5,769,863 A | 6/1998 | Garrison |
| 5,779,727 A | 7/1998 | Orejola |
| 5,788,715 A | 8/1998 | Watson, Jr. et al. |
| 5,792,112 A | 8/1998 | Hart et al. |
| 5,792,151 A | 8/1998 | Heck et al. |
| 5,792,177 A | 8/1998 | Kaseda |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,800,414 A | 9/1998 | Cazal |
| 5,810,845 A | 9/1998 | Yoon |
| 5,814,021 A | 9/1998 | Balbierz |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,843,146 A | 12/1998 | Cross, Jr. |
| 5,855,586 A | 1/1999 | Habara et al. |
| 5,861,005 A | 1/1999 | Kontos |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,906,626 A | 5/1999 | Carrillo |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,993 A | 7/1999 | Yoon |
| 5,921,994 A | 7/1999 | Andreas et al. |
| 5,924,424 A | 7/1999 | Stevens et al. |
| RE36,269 E | 8/1999 | Wright |
| 5,931,787 A | 8/1999 | Dietz et al. |
| 5,941,819 A | 8/1999 | Chin |
| 5,946,688 A | 8/1999 | Roberts |
| 5,947,953 A | 9/1999 | Ash et al. |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,561 A | 4/2000 | Marshall et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,210,416 B1 | 4/2001 | Chu et al. |
| 6,221,007 B1 | 4/2001 | Green |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,292,630 B1 | 9/2001 | Yokonuma |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,312,404 B1 | 11/2001 | Agro et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,338,737 B1 | 1/2002 | Toledano |
| 6,340,356 B1 | 1/2002 | Navia et al. |
| 6,346,074 B1 | 2/2002 | Roth |
| 6,352,503 B1 | 3/2002 | Matsui et al. |
| 6,379,366 B1 | 4/2002 | Fleischman et al. |
| 6,423,051 B1 | 7/2002 | Kaplan et al. |
| 6,461,330 B1 | 10/2002 | Miyagi |
| 6,474,340 B1 | 11/2002 | Vaska et al. |
| 6,485,407 B2 | 11/2002 | Alferness et al. |
| 6,488,664 B1 | 12/2002 | Solomon et al. |
| 6,488,689 B1 | 12/2002 | Kaplan et al. |
| 6,494,211 B1 | 12/2002 | Boyd et al. |
| 6,511,488 B1 | 1/2003 | Marshall et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,616,674 B2 | 9/2003 | Schmieding |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,709,415 B2 | 3/2004 | Navia et al. |
| 6,723,107 B1 | 4/2004 | Skiba et al. |
| 6,733,486 B1 | 5/2004 | Lee et al. |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,855,137 B2 | 2/2005 | Bon |
| 6,932,813 B2 | 8/2005 | Thompson et al. |
| 6,985,776 B2 | 1/2006 | Kane et al. |
| 6,994,092 B2 | 2/2006 | van der Burg et al. |
| 7,011,671 B2 | 3/2006 | Welch |
| 7,041,111 B2 | 5/2006 | Chu |
| 7,044,134 B2 | 5/2006 | Khairkhahan et al. |
| 7,056,294 B2 | 6/2006 | Khairkhahan et al. |
| 7,056,321 B2 | 6/2006 | Pagliuca et al. |
| 7,063,682 B1 | 6/2006 | Whayne et al. |
| 7,063,693 B2 | 6/2006 | Guenst |
| 7,112,172 B2 | 9/2006 | Orban, III et al. |
| 7,128,073 B1 | 10/2006 | Van der Burg et al. |
| 7,135,018 B2 | 11/2006 | Ryan et al. |
| 7,166,099 B2 | 1/2007 | Devens, Jr. |
| 7,169,156 B2 | 1/2007 | Hart |

(56) References Cited

U.S. PATENT DOCUMENTS

| | | |
|---|---|---|
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,722,641 B2 | 5/2010 | van der Burg et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,325 B2 | 3/2015 | Miller et al. |
| 9,089,324 B2 | 7/2015 | McCaw et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark et al. |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0093105 A1 | 5/2003 | Huffmaster |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0068267 A1 | 4/2004 | Harvie et al. |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0070881 A1 | 3/2005 | Gribbons et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0209627 A1 | 9/2005 | Kick et al. |
| 2005/0256532 A1 | 11/2005 | Nayak et al. |
| 2005/0277975 A1 | 12/2005 | Saadat et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0052750 A1 | 3/2006 | Lenker et al. |
| 2006/0100545 A1 | 5/2006 | Ayala et al. |
| 2006/0184107 A1 | 8/2006 | Bencini et al. |
| 2006/0200169 A1 | 9/2006 | Sniffin |
| 2006/0212045 A1 | 9/2006 | Schilling et al. |
| 2006/0235381 A1 | 10/2006 | Whayne et al. |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2006/0264907 A1 | 11/2006 | Eskridge et al. |
| 2006/0270900 A1 | 11/2006 | Chin et al. |
| 2006/0270978 A1 | 11/2006 | Binmoeller et al. |
| 2006/0271032 A1 | 11/2006 | Chin et al. |
| 2007/0010829 A1 | 1/2007 | Nobles et al. |
| 2007/0016165 A1 | 1/2007 | Von Oepen et al. |
| 2007/0016228 A1 | 1/2007 | Salas |
| 2007/0027456 A1 | 2/2007 | Gartner et al. |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015406 A1 | 1/2008 | Dlugos et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0058635 A1 | 3/2008 | Halperin et al. |
| 2008/0097489 A1 | 4/2008 | Goldfarb et al. |
| 2008/0154260 A1 | 6/2008 | Hoof |
| 2008/0177381 A1 | 7/2008 | Navia et al. |
| 2008/0221593 A1 | 9/2008 | Liddicoat et al. |
| 2008/0228265 A1 | 9/2008 | Spence et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |

(56) References Cited

U.S. PATENT DOCUMENTS

| | | |
|---|---|---|
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0082797 A1 | 3/2009 | Fung et al. |
| 2009/0088778 A1 | 4/2009 | Miyamoto et al. |
| 2009/0093809 A1 | 4/2009 | Anderson et al. |
| 2009/0143791 A1 | 6/2009 | Miller et al. |
| 2009/0157118 A1 | 6/2009 | Miller et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund et al. |
| 2010/0174296 A1 | 7/2010 | Vakharia et al. |
| 2010/0191253 A1 | 7/2010 | Oostman et al. |
| 2010/0331820 A1 | 12/2010 | Prisco et al. |
| 2011/0060350 A1 | 3/2011 | Powers et al. |
| 2011/0087247 A1 | 4/2011 | Fung et al. |
| 2011/0087270 A1 | 4/2011 | Penner et al. |
| 2011/0092997 A1 | 4/2011 | Kang |
| 2011/0106107 A1 | 5/2011 | Binmoeller et al. |
| 2011/0112537 A1 | 5/2011 | Bernstein et al. |
| 2011/0144660 A1 | 6/2011 | Liddicoat et al. |
| 2011/0295060 A1 | 12/2011 | Zenati et al. |
| 2012/0022558 A1 | 1/2012 | Friedman et al. |
| 2012/0209300 A1 | 8/2012 | Torrie |
| 2012/0330351 A1 | 12/2012 | Friedman et al. |
| 2013/0144311 A1 | 6/2013 | Fung et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0303721 A1 | 10/2014 | Fung et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2015/0018853 A1 | 1/2015 | Friedman et al. |
| 2015/0025312 A1 | 1/2015 | de Canniere |
| 2015/0119884 A1 | 4/2015 | Fung et al. |
| 2015/0157328 A1 | 6/2015 | Miller et al. |
| 2015/0173765 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Williamson et al. |
| 2015/0250482 A1 | 9/2015 | Slaughter et al. |
| 2015/0272618 A1 | 10/2015 | Fung et al. |
| 2015/0374380 A1 | 12/2015 | Miller et al. |
| 2016/0008001 A1 | 1/2016 | Winkler et al. |
| 2016/0106421 A1 | 4/2016 | Eliachar et al. |
| 2016/0120549 A1 | 5/2016 | Fung et al. |
| 2016/0310144 A1 | 10/2016 | Kimura et al. |
| 2016/0317155 A1 | 11/2016 | Kimura et al. |
| 2016/0346028 A1 | 12/2016 | Rogers et al. |

FOREIGN PATENT DOCUMENTS

| | | |
|---|---|---|
| EP | 0 598 219 A2 | 5/1994 |
| EP | 0 598 219 A3 | 5/1994 |
| EP | 0 598 219 B1 | 5/1994 |
| EP | 0 625 336 A2 | 11/1994 |
| EP | 0 705 566 A1 | 4/1996 |
| EP | 1 010 397 A1 | 6/2000 |
| GB | 1 506 142 A | 4/1978 |
| JP | H-6-319742 A | 11/1994 |
| JP | 7-501959 A | 3/1995 |
| JP | 7-296645 A2 | 11/1995 |
| JP | 7-299073 A | 11/1995 |
| JP | 10-502271 A | 3/1998 |
| JP | 11-501837 A | 2/1999 |
| JP | 11-507262 A | 6/1999 |
| JP | 2001-120560 A | 5/2001 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| WO | WO-93/09722 A1 | 5/1993 |
| WO | WO-94/01045 A1 | 1/1994 |
| WO | WO-94/04079 A1 | 3/1994 |
| WO | WO-94/08514 A1 | 4/1994 |
| WO | WO-96/00531 A1 | 1/1996 |
| WO | WO-96/04854 A1 | 2/1996 |
| WO | WO-96/28098 A1 | 9/1996 |
| WO | WO-96/40356 A1 | 12/1996 |
| WO | WO-96/40368 A1 | 12/1996 |
| WO | WO-97/11644 A1 | 4/1997 |
| WO | WO-97/43957 A1 | 11/1997 |
| WO | WO-98/05289 A1 | 2/1998 |
| WO | WO-98/17187 A1 | 4/1998 |
| WO | WO-99/18878 A2 | 4/1999 |
| WO | WO-99/18878 A3 | 4/1999 |
| WO | WO-00/16850 A1 | 3/2000 |
| WO | WO-00/59383 A1 | 10/2000 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034767 C2 | 4/2005 |
| WO | WO-2005/034802 A2 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2006/116310 A2 | 11/2006 |
| WO | WO-2007/037516 A2 | 4/2007 |
| WO | WO-2007/037516 A3 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/017080 C2 | 2/2008 |
| WO | WO-2008/036408 A2 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |
| WO | WO-2014/164028 A1 | 10/2014 |

OTHER PUBLICATIONS

Advisory Action mailed on Jan. 9, 2006, for U.S. Appl. No. 10/007,364, filed Nov. 5, 2011, 3 pages.

Advisory Action mailed on Feb. 6, 2006, for U.S. Appl. No. 10/105,907, filed Mar. 25, 2002, 2 pages.

Afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

(56) References Cited

OTHER PUBLICATIONS

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.
Bath, P.M.W. et al, (2005). "Current Status of Stroke Prevention in Patients with Atrial Fibrillation," *European Heart Journal Supplements* 7(Supplement C):C12-C18.
Benjamin, B.A. et al. (1994). "Effect of Bilateral Atrial Appendectomy on Postprandial Sodium Excretion in Conscious Monkeys," *Society for Experimental Biology and Medicine* 2006: 1 page.
Beygui, F. et al. (2005, e-pub. Oct. 21, 2005). "Multimodality Imaging of Percutaneous Closure of the Left Atrial Appendage," *Clinical Vignette*, 1 page.
Bisleri, G. et al. (Jun. 3, 2005). "Innovative Monolateral Approach for Closed-Chest Atrial Fibrillation Surgery," *The Annals of Thoracic Surgery* 80:e22-e25.
Björk, V.O. et al. (Aug. 1961). "Sequelae of Left Ventricular Puncture with Angiocardiography," *Circulation* 24:204-212.
Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.
Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.
Bonanomi, G. et al. (Jan. 1, 2003). "Left Atrial Appendectomy and Maze," *Journal of the American College of Cardiology* 41(1):169-171.
Bonow, R.O. et al. (1993). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams (Aug. 11, 2008), "A-Fib: Near a Tipping Point," 167 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1935). "Use of the Surgical Stapler to Obliterate the Left Atrial Appendage," *Surgery, Gynecology & Obstetric* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 37:e45-e47.
Cox, J.L. et al. (Apr. 1991). "The Surgical Treatment of Atrial Fibrillation: IV. Surgical Technique," *J. Thorac. Cardiovasc. Surg.* 101(4):584-592.
Cox, J.L. et al. (Aug. 1995), "Modification of the Maze Procedure for Atrial Rutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003), "Highlights of the Year JACC 2003," *Journal of the American College of Cardiology* 42(12):2156-2166.
Deneu, S. et al. (Jul. 11, 1999) "Catheter Entrapment by Atrial Suture During Minimally Invasive Port-access Cardiac Surgery," *Canadian Journal of Anesthesia* 46(10):983-986.
Deponti, R. et al. (Mar. 7, 2006). "Trans-Septal Catheterization in the Eiectrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1353-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive Midcab Procedure," *Heart Surgery Forum* 2(1):77-81.
European Office Action mailed on Sep. 16, 2010, for European Patent Application No. 08727155.7, filed on Mar. 25, 2008, 5 pages.
European office Action mailed on Aug. 16, 2011, for European Patent Application No. 04794730.4, filed on Oct. 11, 2004, 7 pages.
European Communication mailed on Feb. 5, 2007, for EP Patent Application No. 00957904.6, filed on Aug. 29, 2000, 5 pages.
European Communication mailed on Aug. 8, 2007, for EP Patent Application No. 00957904.6, filed on Aug. 29, 2000, 6 pages.
European Communication mailed on Jul. 14, 2008, for EP Patent Application No. 00957904.6, filed on Aug. 29, 2000, 5 pages.
European Communication mailed on Dec. 23, 2009, for EP Patent Application No. 00957904.6, filed on Aug. 29, 2000, 6 pages.
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.
Final Office Action mailed on Jun. 22, 2009, for U.S. Appl. No. 10/963,371, filed Oct. 11, 2004, 11 pages.
Final Office Action mailed on Apr. 14, 2010, for U.S. Appl. No. 11/600,671, filed Nov. 15, 2006, 7 pages.
Final Office Action mailed on Jul. 21, 2010, for U.S. Appl. No. 11/400,714, filed Apr. 7, 2006, 10 pages.
Final Office Action mailed on Apr. 26, 2011, for U.S. Appl. No. 12/037,802, filed Feb. 26, 2008, 9 pages.
Final Office Action mailed on Sep. 20, 2011, for U.S. Appl. No. 12/212,511, filed Sep. 17, 2008, 8 pages.
Final Office Action mailed on Oct. 28, 2011, for U.S. Appl. No. 12/055,213, filed Mar. 25, 2008, 15 pages.
Final Office Action mailed on May 4, 2012, for U.S. Appl. No. 12/363,359, filed Jan. 30, 2009, 10 pages.
Final Office Action mailed on May 16, 2012, for U.S. Appl. No. 12/363,381, filed Jan. 30, 2009, 8 pages.
Final Office Action mailed on Jul. 11, 2012, for U.S. Appl. No. 13/033,532, filed Feb. 23, 2011, 8 pages.
Final Office Action mailed on Jul. 24, 2012, for U.S. Appl. No. 12/212,511, filed Sep. 17, 2008, 6 pages.
Final Office Action mailed on Oct. 18, 2012, for U.S. Appl. No. 12/124,023, filed May 20, 2008, 15 pages.
Final Office Action mailed on Sep. 23, 2004, for U.S. Appl. No. 10/007,364, filed Nov. 5, 2011, 7 pages.

(56) References Cited

OTHER PUBLICATIONS

Final Office Action mailed on Dec. 21, 2004, for U.S. Appl. No. 10/105,907, filed Mar. 25, 2002, 6 pages.
Final Office Action mailed on Jan. 25, 2005, for U.S. Appl. No. 10/105,984, filed Mar. 25, 2002, 5 pages.
Final Office Action mailed on Feb. 10, 2005, for U.S. Appl. No. 10/105,978, filed Mar. 25, 2002, 7 pages.
Final Office Action mailed on Jul. 19, 2005, for U.S. Appl. No. 10/007,364, filed Nov. 5, 2011, 8 pages.
Final Office Action mailed on Oct. 25, 2005, for U.S. Appl. No. 10/105,907, filed Mar. 25, 2002, 6 pages.
Final Office Action mailed on Mar. 14, 2006, for U.S. Appl. No. 10/105,978, filed Mar. 25, 2002, 8 pages.
Final Office Action mailed on Nov. 1, 2006, for U.S. Appl. No. 10/105,907, filed Mar. 25, 2002, 6 pages.
Final Office Action mailed Aug. 31, 2011, for U.S. Appl. No. 11/944,522, filed Nov. 23, 2007, 7 pages.
Final Office Action mailed Jan. 29, 2013, for U.S. Appl. No. 11/944,522, filed Nov. 23, 2007, 8 pages.
Final Office Action mailed Jan. 7, 2014, for U.S. Appl. No. 11/944,522, filed Nov. 23, 2007, 9 pages.
Final Office Action mailed on Nov. 8, 2013, for U.S. Appl. No. 12/037,802, filed Feb. 26, 2008, 12 pages.
Final Office Action mailed on Jan. 13, 2014, for U.S. Appl. No. 12/752,873, filed Apr. 1, 2010, 10 pages.
Final Office Action mailed on Aug. 12, 2014, for U.S. Appl. No. 13/033,532, filed Feb. 23, 2011, 6 pages.
Final Office Action mailed on Nov. 14, 2014, for U.S. Appl. No. 12/363,359, filed Jan. 30, 2009, 10 pages.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964,.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159:201-208.
Gillinov, A.M. (2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta in Aortography and Renal Arteriography," *Annals of Surgery* 132(5):944-958.
Gottlieb, L.K. et al. (Sep. 12, 1994). "Anticoagulation in Atrial Fibrillation," *Arch Intern Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.
Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (2001) "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," *presented at* The Canadian Cardiovascular Congress 2003, Toronot, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005), "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
International Preliminary Report on Patentability mailed on Oct. 15, 2009, for PCT Application No. PCT/US2008/003938, filed on Mar. 25, 2008, 7 pages.
International Preliminary Report on Patentability mailed on Aug. 12, 2010, for PCT Application No. PCT/US2003/076703, filed on Sep. 17, 2008, 10 pages.
International Search Report mailed on May 19, 2008, for PCT Application No. PCT/US06/013459, filed on Apr. 7, 2006, 1 page.
International Search Report mailed on Feb. 27, 2007, for PCT Application No. PCT/US2008/003938, filed on Mar. 25, 2008, 2 pages.
International Search Report mailed on Jul. 30, 2010, for PCT Application No. PCT/US2008/076703, filed on Sep. 17, 2008, 2 pages.
International Search Report mailed on Jun. 1, 2010, for PCT Application No. PCT/US2010/029668, filed on Apr. 1, 2010, 1 page.
International Search Report mailed on Jan. 19, 2005, for PCT Patent Application No. PCT/US03/14435, filed on May 9, 2003, 4 pages.
International Search Report mailed on Oct. 26, 2000, for PCT Application No. PCT/US2000/023727, filed on Aug. 29, 2000, 1 page.
Jaïs, P. et al. (2003). "Radiofrequency Ablation for Atrial Fibrillation," *European Society of Cardiology* 5(Supplement H):H34-H39.
Japanese Office Action mailed on Nov. 2, 2010, for Japanese Patent Application No. 2006-534449, filed on Oct. 11, 2004, English translation included, 5 pages.
Japanese Office Action mailed on Aug. 23, 2011, for Japanese Patent Application No. 2006-534449, filed on Oct. 11, 2004, English translation, 2 pages.
Japanese Office Action mailed on Mar. 9, 2009.
Japanese Office Action mailed on Feb. 25, 2010, for Japanese Patent Application No. 2002-522787.

(56) References Cited

OTHER PUBLICATIONS

Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6)669-673.
Khargi, K. et al. (2005), "Surgical Treatment of Atrial Fibrillation: A Systematic Review," *European Journal of Cardiothoracic Surgery* 27:258-265.
Kim, K.B. et al. (Jan. 1993). "Effect of the Cox Maze Procedure on the Secretion of Atrial Natriuretic Peptide," *J. Thorac. Cardiovasc. Surg.* 115(1)139-146; discussion 146-147.
Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.
Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multidimensional Imaging of the Human Left Atrial Appendage," *Europace* 9:1134-1140.
Lee, R. et al. (1999). "The Closed Heart MAZE: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 31:23-26.
Li, H. (2007). "Magnet Decoration, Beautiful But Potentially Dangerous for Patients with Implantable Pacemakers or Defibrillators," *Heart Rhythm* 4(1):5-6.
Lindsay, B.D. (1996). "Obliteration of the Left Atrial Appendage: a Concept Worth Testing," *The Annals of Thoracic Surgery* 61:515.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):431-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com, last visited on Apr. 7, 2009, 73:746-751.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008), "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.
Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.
Non-Final Office Action mailed on Aug. 6, 2008 for U.S. Appl. No. 10/963,371, filed Oct. 11, 2004, 14 pages.
Non-Final Office Action mailed on Jun. 26, 2009, for U.S. Appl. No. 11/600,671, filed Nov. 15, 2006, 9 pages.
Non-Final Office Action mailed on Dec. 30, 2009, for U.S. Appl. No. 11/400,714, filed Apr. 7, 2006, 8 pages.
Non-Final Office Action mailed on Jul. 22, 2010, for U.S. Appl. No. 12/037,802, filed Feb. 26, 2008, 10 pages.
Non-Final Office Action mailed on Nov. 15, 2010, for U.S. Appl. No. 12/055,213, filed Mar. 25, 2008, 18 pages.
Non-Final Office Action mailed on Feb. 17, 2011, for U.S. Appl. No. 12/212,511, filed Sep. 17, 2008, 14 pages.
Non-Final Office Action mailed on Apr. 23, 2011, for U.S. Appl. No. 12/055,213, filed Mar. 25, 2008, 20 pages.
Non-Final Office Action mailed on Oct. 27, 2011, for U.S. Appl. No. 12/363,359, filed Jan. 30, 2009, 11 pages.
Non-Final Office Action mailed on Nov. 9, 2011, for U.S. Appl. No. 12/363,381, filed Jan. 30, 2009, 10 pages.

(56) References Cited

OTHER PUBLICATIONS

Non-Final Office Action mailed on Dec. 22, 2011, for U.S. Appl. No. 13/033,532, filed Feb. 23, 2011, 8 pages.
Non-Final Office Action mailed on Mar. 7, 2012, for U.S. Appl. No. 12/124,023, filed May 20, 2008, 13 pages.
Non-Final Office Action mailed on Apr. 2, 2012, for U.S. Appl. No. 12/212,511, filed Sep. 17, 2008, 5 pages.
Non-Final Office Action mailed on Jul. 10, 2012, for U.S. Appl. No. 11/944,522, filed Nov. 23, 2007, 8 pages.
Non-Final Office Action mailed on Mar. 13, 2008 for U.S. Appl. No. 10/963,371, filed Oct. 11, 2004, 13 pages.
Non-Final Office Action mailed on Dec. 31, 2003, for U.S. Appl. No. 10/105,984, filed Mar. 25, 2002, 5 pages.
Non-Final Office Action mailed on Mar. 16, 2004, for U.S. Appl. No. 10/007,364, filed Nov. 5, 2011, 6 pages.
Non-Final Office Action mailed on Jun. 17, 2004, for U.S. Appl. No. 10/105,978, filed Mar. 25, 2002, 6 pages.
Non-Final Office Action mailed on Jun. 28, 2004, for U.S. Appl. No. 10/105,907, filed Mar. 25, 2002, 5 pages.
Non-Final Office Action mailed on Aug. 6, 2004, for U.S. Appl. No. 10/105,984, filed Mar. 25, 2002, 5 pages.
Non-Final Office Action mailed on Aug. 18, 2004, for U.S. Appl. No. 10/105,978, filed Mar. 25, 2002, 6 pages.
Non-Final Office Action mailed on Feb. 8, 2005, for U.S. Appl. No. 10/007,364, filed Nov. 5, 2011, 6 pages.
Non-Final Office Action mailed on May 11, 2005, for U.S. Appl. No. 10/105,907, filed Mar. 25, 2002, 7 pages.
Non-Final Office Action mailed on Jun. 2, 2005, for U.S. Appl. No. 10/105,984, filed Mar. 25, 2002, 4 pages.
Non-Final Office Action mailed on Jul. 20, 2005, for U.S. Appl. No. 10/105,978, filed Mar. 25, 2002, 6 pages.
Non-Final Office Action mailed on Feb. 16, 2006, for U.S. Appl. No. 10/105,984, filed Mar. 25, 2002, 6 pages.
Non-Final Office Action mailed on Mar. 29, 2006, for U.S. Appl. No. 10/007,364, filed Nov. 5, 2011, 8 pages.
Non-Final Office Action mailed on May 2, 2006, for U.S. Appl. No. 10/105,907, filed Mar. 25, 2002, 6 pages.
Non-Final Office Action mailed on Jul. 27, 2006, for U.S. Appl. No. 10/105,984, filed Mar. 25, 2002, 5 pages.
Non-Final Office Action mailed on Jan. 25, 2007, for U.S. Appl. No. 10/105,978, filed Mar. 25, 2002, 9 pages.
Non-Final Office Action mailed on Apr. 12, 2010, for U.S. Appl. No. 11/944,522, filed Nov. 23, 2007, 6 pages.
Non-Final Office Action mailed on Dec. 15, 2010, for U.S. Appl. No. 11/944,522, filed Nov. 23, 2007, 6 pages.
Non-Final Office Action mailed on Aug. 9, 2013, for U.S. Appl. No. 11/944,522, filed Nov. 23, 2007, 8 pages.
Non-Final Office Action mailed on Sep. 18, 2013, 2011, for U.S. Appl. No. 12/055,213, filed Mar. 25, 2008, 15 pages.
Non-Final Office Action mailed on May 31, 2013, for U.S. Appl. No. 12/124,023, filed May 20, 2008, 14 pages.
Non-Final Office Action mailed on Apr. 2, 2014, for U.S. Appl. No. 13/033,532, filed Feb. 23, 2011, 8 pages.
Non-Final Office Action mailed on Jul. 1, 2014, for U.S. Appl. No. 11/944,522, filed Nov. 23, 2007, 9 pages.
Non-Final Office Action mailed on Jun. 17, 2014, for U.S. Appl. No. 12/363,359, filed Jan. 30, 2009, 7 pages.
Non-Final Office Action mailed on Nov. 10, 2014, for U.S. Appl. No. 12/752,873, filed Apr. 1, 2010, 10 pages.
Notice of Allowance mailed on Aug. 15, 2006, for U.S. Appl. No. 10/105,978, filed Mar. 25, 2002, 7 pages.
Notice of Allowance mailed on Sep. 12, 2006, for U.S. Appl. No. 10/007,364, filed Nov. 5, 2011, 7 pages.
Notice of Allowance mailed on Feb. 12, 2007, for U.S. Appl. No. 10/007,364, filed Nov. 5, 2011, 7 pages.
Notice of Allowance mailed on Sep. 18, 2007, for U.S. Appl. No. 10/105,978, filed Mar. 25, 2002, 8 pages.
Notice of Allowance mailed on Dec. 26, 2013, for U.S. Appl. No. 13/160,441, filed Jun. 14, 2011, 9 pages.
Notice of Allowance mailed on Sep. 17, 2010, for U.S. Appl. No. 10/963,371, filed Oct. 11, 2004, 7 pages.
Notice of Allowance mailed on Sep. 17, 2010, for U.S. Appl. No. 11/600,671, filed Nov. 15, 2006, 7 pages.
Notice of Allowance mailed on Nov. 24, 2010, for U.S. Appl. No. 11/400,714, filed Apr. 7, 2006, 8 pages.
Notice of Allowance mailed on Feb. 22, 2013, for U.S. Appl. No. 12/212,511, filed Sep. 17, 2008, 8 pages.
Notice of Allowance mailed on Mar. 18, 2013, for U.S. Appl. No. 12/212,511, filed Sep. 17, 2008, 4 pages.
Notice of Allowance mailed on Mar. 4, 2014, for U.S. Appl. No. 12/055,213, filed Mar. 25, 2008, 9 pages.
Notice of Allowance mailed on Apr. 1, 2014, for U.S. Appl. No. 12/363,381, filed Jan. 30, 2009, 9 pages.
Notice of Allowance mailed on Apr. 3, 2014, for U.S. Appl. No. 12/037,802, filed Feb. 26, 2008, 8 pages.
Notice of Allowance mailed on Oct. 24, 2014, for U.S. Appl. No. 11/944,522, filed Nov. 23, 2007, 8 pages.
Notice of Allowance mailed on Dec. 29, 2014, for U.S. Appl. No. 12/363,381, filed Jan. 30, 2009, 9 pages.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003), "Percutaneous Closure of the Left Atrial Appendage," *Journal of Interventional Cardiology* 16(6):553-556.
Ota, T. et al. (2006), "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134:982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick, C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987), "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.

(56) References Cited

OTHER PUBLICATIONS

Salzberg, S.P. at al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009), "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005), "Epicardial Access: Present and Future Applications for Interventional Electrophysiologists," Chapter 25 in *New Arrhythmia Technolgies*, Wang, P.J.ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I)I-30-I-35.

Sengupta, P.P. et al. (2005), "Transoesophageal Echocardiography," *Heart* 91:541-547.

Sharada, K. et al. (2005), "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (Sep. 7, 2004; e-pub. Aug. 30, 2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005), "Epicardial Mapping and Ablation Techniques to Control Centricular Tachycardia," *Journal of Cardiovasc. Electrphsiol.* 16(4):449-452.

Sparks, P.B. et al. (Sep. 2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During vol. Loading in Conscious Dogs," *Circulation Research* 70(4)124-732.

Stewart, S. (1974), "Placement of the Sutureless Epicardial Pacemaker Lead by the Subxiphoid Approach," *Ann. of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003), "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

Su, P. et al, (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: two-Year Clinical Experience," *Ann. Thorac. Surg.* 64(6):1643-1653, Abstract Only.

Suehiro, S. et al. (1996). "Echocardiography-Guided Pericardiocentesis With a Needle Attached to a Probe," *Ann. Thoracic Surg.* 61:741-742.

Sun, F. et al. (Feb. 2006). "Subxiphoid Access to Normal Pericardium with Micropuncture Set: Technical Feasibility Study in Pigs," *Radiology* 238(2):719-724.

Supplementary European Search Report mailed on Aug. 14, 2006, for EP Patent Application No. 00957904.6, filed on Aug. 29, 2000, 6 pages.

Supplemental Notice of Allowance mailed on Oct. 6, 2006, for U.S. Appl. No. 10/007,364, filed Nov. 5, 2011, 9 pages.

Supplemental Notice of Allowance mailed on Oct. 6, 2006, for U.S. Appl. No. 10/105,978, filed Mar. 25, 2002, 2 pages.

Supplemental Notice of Allowance mailed on Feb. 27, 2007, for U.S. Appl. No. 10/007,364, filed Nov. 5, 2011, 4 pages.

Szili-Torok, T. et al. (2001). "Transseptal Left heart Catheterisation Guided by Intracardiac Echocardiography," *Heart* 86:e11-e15.

Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992), "Conjoined Subrectus Pocket for Permanent Pacemaker Placement in the Neonate," *Ann Thorac Surg.* 53(6):1130-1131, Abstract Only.

Valderrabano, M. et al. (Sep. 2004), "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *American Medical Association* 290(8):1049-1056.

(56) References Cited

OTHER PUBLICATIONS

Watkins, L. et al. (Nov. 1982). "Implantation of the Automatic Defibrillator: The Subxiphoid Approach," *Ann. of Thoracic Surg.* 34(5):515-520.

W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor for Stroke: The Framingham Study," *Stroke* 22(8):983-988.

Wolf, P.A. et al. (Feb. 9, 1998). "Impact of Atrial Fibrillation on Mortality, Stroke, and Medical Costs," *Arch Intern Med* 158:229-234.

Wong, J.W.W. et al. (2006). "Impact of Maze and Concomitant Mitral Valve Surgery on Clinical Outcomes," *The Annals of Thoracic Surgery* 82:1938-1947.

Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.

Wood, M.A. (Jan. 2006). "Percutaneous Pericardial Instrumentation in the Electrophysiology Laboratory: A Case of Need," *Heart Rhythm* 3(1):11-12.

Written Opinion mailed on May 19, 2008, for PCT Application No. PCT/US06/013459, filed on Apr. 7, 2006, 6 pages.

Written Opinion of the International Searching Authority mailed on Feb. 27, 2007, for PCT Application No. PCT/US2008/003938, filed on Mar. 25, 2008, 10 pages.

Written Opinion of the International Searching Authority mailed on Jul. 30, 2010, for PCT Application No. PCT/US2008/076703, filed on Sep. 17, 2008, 8 pages.

Written Opinion of the International Searching Authority mailed on Jun. 1, 2010, for PCT Application No. PCT/US2010/029668, filed on Apr. 1, 2010, 8 pages.

Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.

Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.

Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.

Zapolanski, A. et al. (May 2008). "Safe and Complete Exclusion of the left Atrial Appendage, A Simple Epicardial Approach," *Innovations* 3(3):161-163.

Zenati, M.A. et al. (Sep. 2003). "Left Heart Pacing Lead Implantation Using Subxiphoid Videopericardioscopy," *Journal of Cardiovascular Electrophysiology* 14(9):949-953.

Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.

Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.

U.S. Appl. No. 14/625,540, filed Feb. 18, 2015, for Miller et al.

Final Office Action mailed on Apr. 1, 2016, for U.S. Appl. No. 13/033,532, filed Feb. 23, 2011, 8 pages.

Final Office Action mailed on Mar. 17, 2016, for U.S. Appl. No. 12/363,359, filed Jan. 30, 2009, 10 pages.

Final Office Action mailed on Oct. 22, 2013, for U.S. Appl. No. 13/086,390, filed Apr. 13, 2011, 6 pages.

Final Office Action mailed Nov. 18, 2015, for U.S. Appl. No. 13/490,919, filed Jun. 7, 2012, 10 pages.

Non-Final Office Action mailed on Jan. 16, 2013, for U.S. Appl. No. 12/037,802, filed Feb. 26, 2008, 10 pages.

Non-Final Office Action mailed on May 4, 2015, for U.S. Appl. No. 12/124,023, filed May 20, 2008, 8 pages.

Non-Final Office Action mailed on Oct. 28, 2015, for U.S. Appl. No. 13/033,532, filed Feb. 23, 2011, 9 pages.

Non-Final Office Action mailed on Sep. 10, 2015, for U.S. Appl. No. 12/363,359, filed Jan. 30, 2009, 13 pages.

Non-Final Office Action mailed on Feb. 5, 2014 for U.S. Appl. No. 13/086,389, filed Apr. 13, 2011, 16 pages.

Non-Final Office Action mailed on Jan. 15, 2015, for U.S. Appl. No. 13/086,389, filed Apr. 13, 2011, 16 pages.

Non-Final Office Action mailed on May 3, 2013, for U.S. Appl. No. 13/086,390, filed Apr. 13, 2011, 10 pages.

Non-Final Office Action mailed on Dec. 2, 2015, for U.S. Appl. No. 14/309,835, filed Jun. 19, 2014, 8 pages.

Non-Final Office Action mailed Mar. 31, 2015, for U.S. Appl. No. 13/490,919, filed Jun. 7, 2012, 14 pages.

Notice of Allowance mailed on Oct. 21, 2015, for U.S. Appl. No. 12/124,023, filed May 20, 2008, 9 pages.

Notice of Allowance mailed on Jul. 22, 2015, for U.S. Appl. No. 12/752,873, filed Apr. 1, 2010, 8 pages.

Notice of Allowance mailed on Mar. 20, 2014 for U.S. Appl. No. 13/086,390, filed Apr. 13, 2011, 8 pages.

Notice of Allowance mailed Apr. 11, 2016, for U.S. Appl. No. 14/195,797, filed Mar. 3, 2014, 14 pages.

Notice of Allowance mailed Jul. 19, 2016, for U.S. Appl. No. 13/490,919, filed Jun. 7, 2012, 10 pages.

U.S. Appl. No. 15/080,410, filed Mar. 24, 2016, by Fung et al.

U.S. Appl. No. 15/080,398, filed Mar. 24, 2016, by Fung et al.

Extended European Search Report mailed on Jun. 9, 2015, for EP Application No. 12 797 543.1, filed on Jun. 7, 2012, 6 pages.

Extended European Search Report mailed on Oct. 14, 2016, for EP Application No. 14 779 388.9 filed on Mar. 3, 2014, 8 pages.

Extended European Search Report mailed on Feb. 10, 2017, for EP Application No. 10 759 425.1, filed on Apr. 1, 2010, 7 pages.

International Search Report mailed on Oct. 3, 2011, for PCT Patent Application No. PCT/US2011/00677, filed on Apr. 13, 2011, 5 pages.

International Search Report mailed on Sep. 14, 2012, for PCT Patent Application No. PCT/US2012/41285, filed on Jun. 7, 2012, 2 pages.

International Search Report mailed on Aug. 8, 2014, for PCT Application No. PCT/US2014/020030, filed on Mar. 3, 2014, 4 pages.

Non-Final Office Action mailed on Dec. 2, 2016, for U.S. Appl. No. 14/625,540, filed Feb. 18, 2015, 20 pages.

Supplementary Search Report mailed on Mar. 14, 2011, for EP Application No. 04 794 730.4, filed on Oct. 11, 2004, 4 pages.

Written Opinion of the International Searching Authority mailed on Jul. 13, 2011, for PCT Patent Application No. PCT/US2011/000676, filed on Apr. 13, 2011, 6 pages.

Written Opinion of the International Search Authority mailed on Oct. 3, 2011, for PCT Application No. PCT/US2011/00677, filed on Apr. 13, 2011, 6 pages.

Written Opinion from the International Searching Authority mailed on Sep. 14, 2012, for PCT Patent Application No. PCT/US2012/41285, filed on Jun. 7, 2012, 6 pages.

Written Opinion of the International Searching Authority mailed on Aug. 8, 2014, for PCT Application No. PCT/US2014/020030, filed on Mar. 3, 2014, 6 pages.

\* cited by examiner

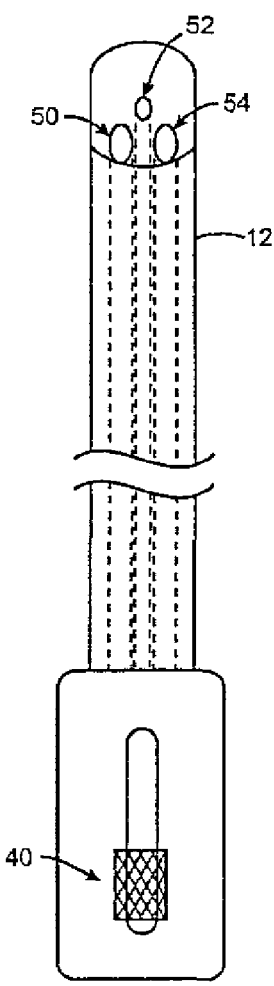
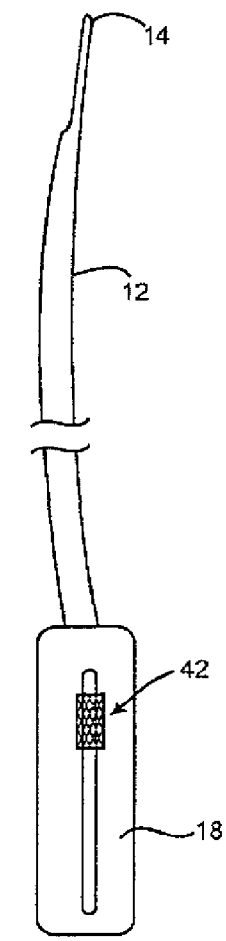
FIG. 4C
FIG. 4A   FIG. 4B

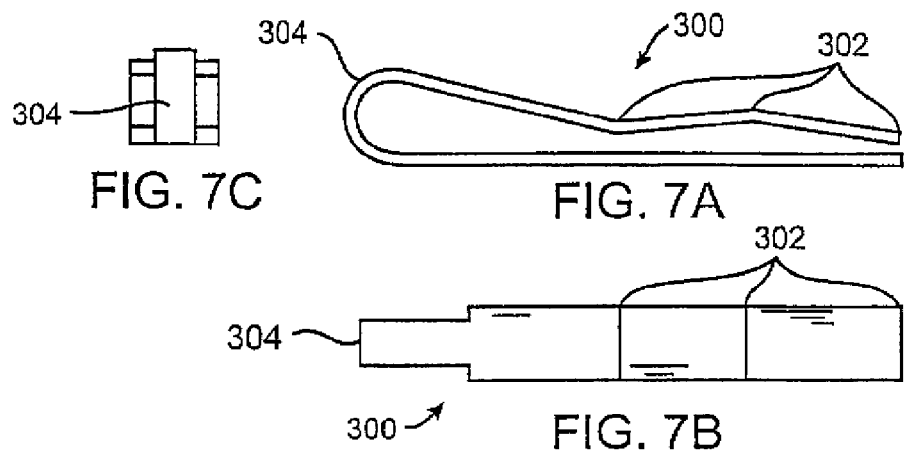
FIG. 7C    FIG. 7A
FIG. 7B
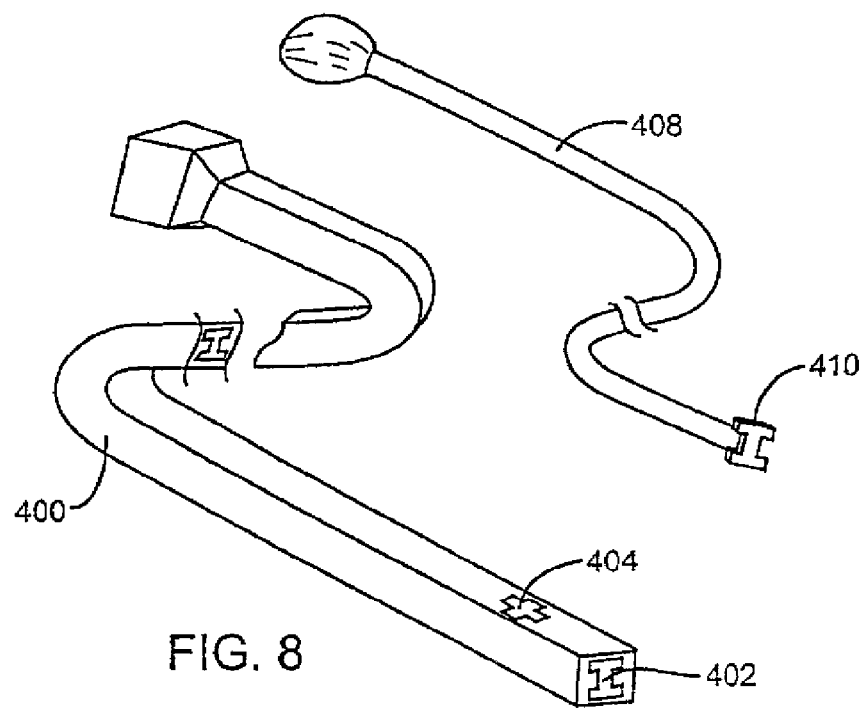
FIG. 8

METHODS AND APPARATUS FOR TRANSPERICARDIAL LEFT ATRIAL APPENDAGE CLOSURE

CROSS-REFERENCE TO RELATED APPLICATIONS

The present application is a continuation of U.S. patent application Ser. No. 11/944,522, filed Nov. 23, 2007, which is a continuation of U.S. patent application Ser. No. 10/105,978, filed Mar. 25, 2002, which issued as U.S. Pat. No. 7,318,829 on Jan. 15, 2008, which is a divisional of U.S. patent application Ser. No. 10/007,364, filed Nov. 5, 2001, which issued as U.S. Pat. No. 7,226,458 on Jun. 5, 2007, which is a divisional of U.S. patent application Ser. No. 09/315,601, filed May 20, 1999, which issued as U.S. Pat. No. 6,488,689 on Dec. 3, 2002.

BACKGROUND OF THE INVENTION

1. Field of the Invention

The present invention relates generally to medical methods and apparatus. More particularly, the present invention relates to a method and device for the minimally invasive closure of a left atrial appendage of the heart.

Atrial fibrillation is a common cardiac rhythm disorder affecting a population of approximately 2.5 million patients in the United States alone. Atrial fibrillation results from a number of different causes and is characterized by a rapid chaotic heart beat. In addition to the risks associated with a disordered heart beat, patients with atrial fibrillation also have an increased risk of stroke. It has been estimated that approximately 75,000 atrial fibrillation patients each year suffer a stroke related to that condition. It appears that strokes in these patients result from emboli many of which may originate from the left atrial appendage. The irregular heart beat causes blood to pool in the left atrial appendage, allowing clots to accumulate over time. From time to time, clot may dislodge from the left atrial appendage and may enter the cranial circulation causing a stroke, the coronary circulation causing a myocardial infarction, the peripheral circulation causing limb ischemia, as well as other vascular beds.

Significant efforts have been made to reduce the risk of stroke in patients suffering from atrial fibrillation. Most commonly, those patients are treated with blood thinning agents, such as coumadin, to reduce the risk of clot formation. While such treatment can significantly reduce the risk of stroke, it also increases the risk of bleeding and for that reason is inappropriate for many atrial fibrillation patients.

As an alternative to drug therapy, surgical procedures for closing the left atrial appendage have been proposed. Most commonly, the left atrial appendage has been closed or removed in open surgical procedures, typically where the heart has stopped and the chest opened through the sternum. Because of the significant risk and trauma of such procedures, left atrial appendage removal occurs almost exclusively when the patient's chest is opened for other procedures, such as coronary artery bypass or valve surgery.

For that reason, alternative procedures which do not require opening of the patient's chest, i.e., a large median sternotomy, have been proposed. U.S. patent No. 3,306,234 to Johnson describes a thoracoscopic procedure where access to the pericardial space over the heart is achieved using a pair of intercostal penetrations (i.e., penetrations between the patient's ribs) to establish both visual and surgical access. While such procedures may be performed while the heart remains beating, they still require deflation of the patient's lung and that the patient be placed under full anesthesia. Furthermore, placement of a chest tube is typically required to reinflate the lung, often requiring a hospitalization for a couple of days.

U.S. Pat. No. 5,865,791, to Whayne et al. describes a transvascular approach for closing the left atrial appendage. Access is gained via the venous system, typically through a femoral vein, a right internal jugular vain, or a subclavian vein, where a catheter is advanced in an antegrade direction to the right atrium. The intra-atrial septum is then penetrated, and the catheter passed into the left atrium. The catheter is then positioned in the vicinity of the left atrial appendage which is then fused closed, e.g., using radiofrequency energy, ether electrical energy, thermal energy, surgical adhesives, or the like. Whayne et al. further describes a thoracoscopic procedure where the pericardium is penetrated through the rib cage and a lasso placed to tie off the neck of the left atrial appendage. Other fixation means described include sutures, staples, shape memory wires, biocompatible adhesives, tissue ablation, and the like. The transvascular approach, suggested by Whayne et al. is advantageous in that it avoids the need to penetrate the patient's chest but suffers from the need to penetrate the intra-atrial septum, may not provide definitive closure, requires entry into the left atrial appendage which may dislodge clot and requires injury to the endocardial surface which may promote thrombus formation. A thoracoscopic approach which is also suggested by Whayne et al. suffers from the same problems as the thoracoscopic approach suggested by Johnson.

For all these reasons, it would be desirable to provide improved and alternative methods and procedures for performing minimally invasive closure of the left atrial appendage. Such methods and procedures will preferably be capable of being performed on patients who have received only a local anesthetic and whose hearts have not been stopped. It would be further desirable to provide methods and procedures which approach the left atrial appendage without the need to perform a thoracotomy (penetration through the intracostal space) or the need to perform a transeptal penetration and/or perform the procedure within the left atrium or left atrial appendage. More specifically, it would be preferable to provide methods and procedures which permitted access to the pericardial space from the xiphoid region of a patient's chest. In addition to the improved and alternative methods and procedures, it would be desirable to provide specialized instruments, devices, and systems for accessing a region over a patient's left atrial appendage from a sub-xiphoid access point to permit closure of the left atrial appendage.

At least some of these objectives will be met by the inventions described herein below.

2. Description of the Background Art

U.S. Pat. Nos. 5,306,234 and 5,865,791 have been described above. U.S. Pat. No. 3,496,932 and PCT publication WO 98/05289 describe methods and apparatus which employ a sub-xiphoid approach for direct cardiac massage.

SUMMARY OF THE INVENTION

The present invention provides alternative and improved methods and apparatus for closing a left atrial appendage of a patient, particularly a patient at risk of occlusive stroke resulting from emboli released from the left atrial appendage. The most likely patient population for the procedures will be patients suffering from atrial fibrillation which can result in clot and thrombus generation in the left atrial appendage, as described above. The methods and apparatus of the present invention permit procedures to be performed on a conscious sedated patient, often in an ambulatory surgical setting where the patient may be released shortly after the procedure is completed. In particular, the methods and apparatus of the present invention eliminates the need for a large incision and division of the sternum, i.e., median sternotomy. The present invention further eliminates the need to take down (deflate) a lung to access a left atrial appendage, as is usually required in thoracoscopic procedures performed via intracostal access.

The methods of the present invention will be performed in a minimally invasive manner, i.e., where access to the pericardial space overlying the patient's left atrial appendage is accomplished through percutaneous penetrations through the patient's skin. Rather than passing through the rib cage, as with prior thoracoscopic techniques, the present invention relies on a "sub-xiphoid" approach where the percutaneous penetration is first made beneath the rib cage, preferably between the xiphoid and adjacent costal cartilage, and an atrial appendage closure tool advanced through the penetration, over the epicardial surface (in the pericardial space) to reach a location adjacent to the exterior of the left atrial appendage. The closure tool can then be used to close the left atrial appendage to prevent the formation of clot and the release of emboli from the atrium.

Closure can be effected in a variety of ways. It is presently preferred to position a loop of material, such as suture, wire, mesh, tape, or the like, over the appendage and cinch the loop tighter to close the interior of the appendage. A variety of alternative closure techniques would also find use, including suturing (using remotely actuated suturing instruments), stapling, clipping, fusing, gluing, clamping, riveting, or the like. Such closure will generally be intended to be permanent, i.e., it will remain indefinitely after the closure tool is removed, but in some instances could be reversible, i.e., the left atrial appendage could be reopened on a subsequent procedure.

Thus, a method according to the present invention for closing a left atrial appendage of a patient's heart comprises positioning a closure instrument through a percutaneous passage beneath the rib cage, over an epicardial surface, and adjacent to the left atrial appendage. The left atrial appendage is then closed, usually using one of the techniques described above. The positioning step may comprise making an incision usually between a costal cartilage and a xiphoid of the patient, establishing a tract beneath the rib cage. Alternatively the incision may be made superficial to the xiphoid or sternum after which a tract is made through the rib cage to the pericardial space, and will preferably include placing an access sheath through the incision into the pericardial space. The incision may be made using a scalpel or other conventional surgical tool, but could also be made using a trocar and cannula assembly, such as those used in laparoscopic surgery, where the trocar could then be removed leaving the cannula in place as the sheath of the present invention. Use of a trocar and cannula may be less preferred, however, since there is an increased risk of injuring the heart if the trocar and cannula assembly is introduced in a blind fashion.

A closure instrument is then introduced through the sheath into the pericardial space, and over an epicardial surface to the exterior of the left atrial appendage, as described above. Preferably, a distal end of the tool will be introduced into an atrioventricular groove which lies just beneath the atrial appendage.

Preferably, once the closure tool has been introduced, advancement and positioning can be performed under conventional imaging techniques, such as fluoroscopic imaging. Often, the closure tool will include or be compatible with imaging scopes which may be introduced through the tool. The use of imaging scopes will be particularly useful during the closure procedure where the left atrial appendage is manipulated as described in more detail below. In such instances, it will frequently be desirable to introduce a saline or other clear fluid into the pericardial space to facilitate viewing.

Once the closure tool is properly positioned, closure may be effected by any of the techniques described above, including looping, suturing, stapling, clipping, fusing, clamping, riveting, or the like. Preferably, the closure will be directed at the base region of the left atrial appendage. Optionally, closing the appendage may further comprise grasping the exterior of the left atrial appendage prior to the actual closing step. Grasping will typically be performed with the conventional grasping tool. As described below, a preferred closure technique is to first grasp the exterior of the left atrial appendage with a grasping tool and subsequently advance a closure loop over the tool on to the exterior of the appendage. A closure loop may then be cinched or otherwise closed or allowed to close, and the tools removed.

A variety of specific instruments, devices, and systems may be devised for performing the methods of the present invention. An exemplary device for closing a left atrial appendage according to the methods of the present invention is described in detail in the descriptions that follow. The device comprises a shaft having a proximal end and a distal end, where the distal end is adapted to percutaneously enter the pericardial space, be advanced over an epicardial surface, and then approach the exterior of the left atrial appendage. Preferably, the shaft has a length in the range from 10 cm to 40 cm, a width in the range from 2 mm to 20 mm, and a thickness in the range from 1 mm to 10 mm. Usually, the shaft will be curved over its length to be compatible with the curvature of the heart. The shaft may include a means to alter the curvature to accommodate variations in anatomy. Similarly, the device may preferably include a crescent-shaped cross-section to also conform to the shape of the exterior of the heart. The device will carry a mechanism or means for closing the left atrial appendage when the distal end of the shaft is positioned adjacent to the appendage. Usually, the closure mechanism will be introducable through one or more lumens formed in the shaft. In a particularly preferred configuration, the distal end of the shaft will be configured to lie within the atrioventricular groove of the heart, and at least one lumen through the shaft will have an exit port spaced inwardly from the distal end of the shaft by a distance in the range from 0.5 cm to 5 cm. In this way, the port will be positioned properly to access the free end of the atrial appendage for performing the closing procedures. In addition, the shaft may have one or more additional lumens (for a total of two, three, or more lumens through the shaft) in order to provide additional capabilities, including introduction and use of a viewing scope, infusion and perfusion of fluids, particularly the infusion of saline to facilitate viewing. Optionally, the lumens can be used to introduce an anesthetic agent, such as lidocaine, in order to reduce pain or to introduce an anti-arrhythmic agent to reduce myocardial irritability.

The present invention still further comprises kits including the closure devices just described. The kits will further include instructions for use according to the methods described above, and optionally further include packaging for holding all components of the kit together. Additionally, the kits may include the access sheath which is placed through the percutaneous penetration tracks as the pericardial space. The access sheath may be in the form of a trocar and cannula assembly, although this will usually not be preferred.

BRIEF DESCRIPTION OF THE DRAWINGS

FIGS. 4A-4C are orthogonal views of the closure device of FIG. 3.

FIG. 7A-7C illustrate an exemplary clip which may be used in performing the closure methods of the present invention.

FIG. 8 illustrates a clip insertion tool useful for placing the clip of FIGS. 7A-7C according to the methods of the present invention.

DESCRIPTION OF THE SPECIFIC EMBODIMENTS

Figure 1:
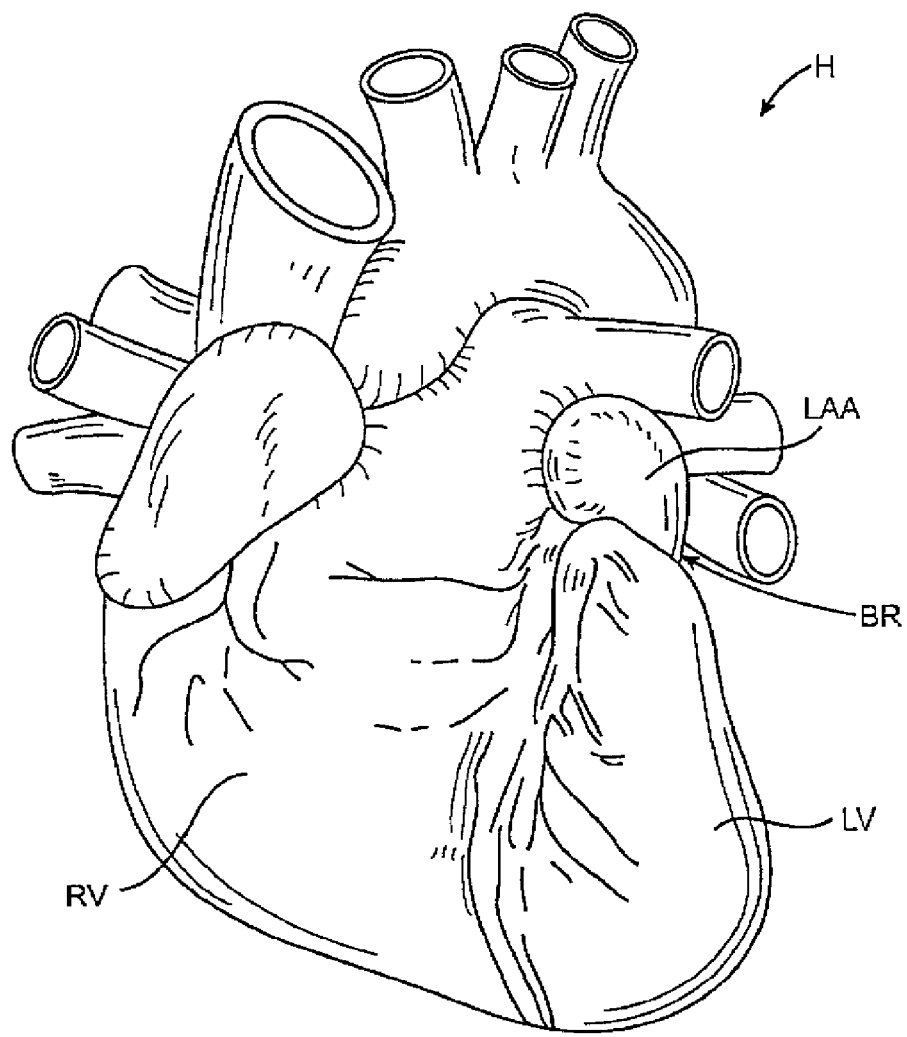
FIG. 1 is an anterior view of a heart illustrating the position of the left atrial appendage relative to the remaining structures of the heart.

FIG. 1 is an anterior view of a heart illustrating the right ventricle RV, the left ventricle LV, and the left atrial appendage LAA. The methods and apparatus of the present invention are intended to place a closure structure over or otherwise close of the base region BR of the left atrial appendage. By closing off the base region BR, the exchange of materials between the left atrial appendage LAA and the left atrium LA will be stopped. Thus, the release of emboli from the left atrial appendage into the left atrium will be stopped.

Figure 2:
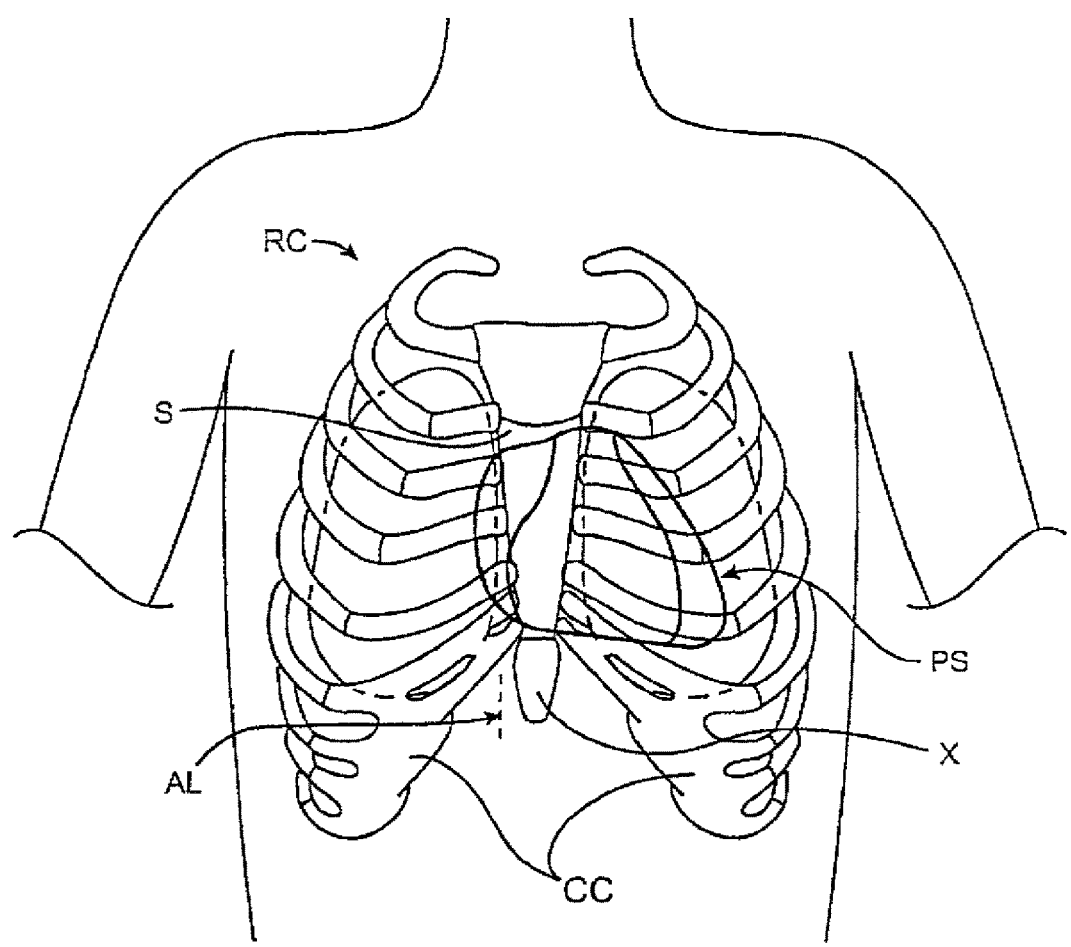
FIG. 2 shows the position of the heart in an associated chest cavity and illustrates a preferred percutaneous access site for performing the methods of the present invention.

Referring now to FIG. 2, the heart is located within the pericardial space PS located beneath the patient's rib cage RC. The sternum S is located in the center of the rib cage RC and terminates at its lower end in the xiphoid X. On either side of the xiphoid are the costal cartilage CC, and the percutaneous access points for performing the procedures of the present invention will be located beneath the rib cage RC, and preferably between the xiphoid X and an adjacent costal cartilage CC, preferably at the access location AL shown by a broken line.

An exemplary tool 10 for performing the methods of the present invention is illustrated in FIGS. 3, 3A, and 4A-4C. The tool comprises a shaft 12 having a distal end 14 and a proximal end 16. A handle 18 is preferably attached to the proximal end of the shaft, and the shaft will have a curved profile in its axial direction (as best seen in FIG. 4B) and a crescent-shaped cross-section, as best seen in FIG. 4C. The preferred dimensions of the shaft are set forth above.

In the illustrated embodiment, the shaft has three lumens 20, 22, and 24. A first lumen 20 is used for introducing a closure tool (which may be any of the closure tools described above), while the second and third lumens (22 and 24, respectively) are used for introducing a viewing scope and fluids, such as saline or other clear fluids for improving visualization of the region surrounding the left atrial appendage. In alternative embodiments, the first lumen 20 can still be used for a grasper, while either of the second lumen 22 and/or third lumen 24 may be used for introducing alternative closure devices, such as clip appliers, riveting devices, fusing devices, suturing devices, stapling devices, or the like. In a particular embodiment shown below, either or both of the lumens 22 and 24 may be used to advance a clip over the left atrial appendage as the appendage is being grasped by a grasper, such as the one shown in FIG. 3.

Figure 3A:
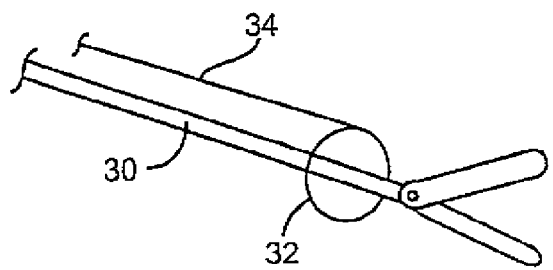
FIGS. 3 and 3A are perspective views of an exemplary closure tool useful for performing the methods of the present invention.
Figure 3:
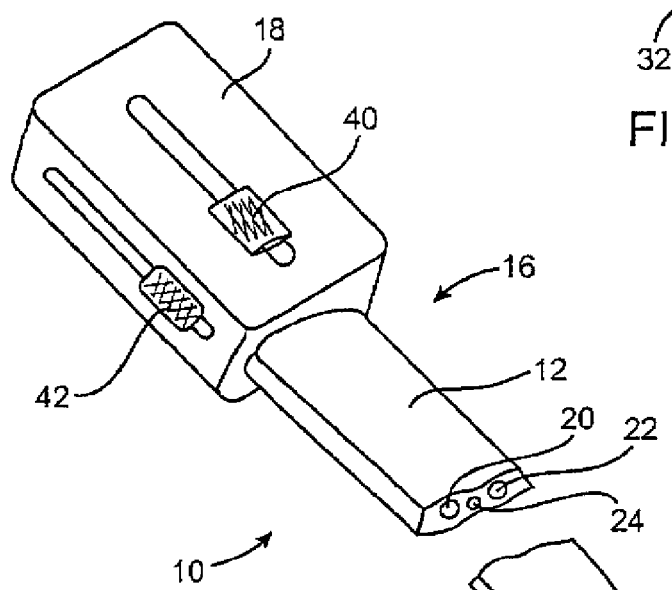
Figure 3:
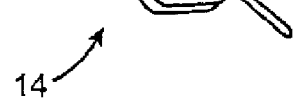

While the closure tool may have any of a wide variety of designs, the presently preferred tool, is shown in FIG. 3A. The tool comprises a grasper 30 and a capture loop 32. Capture loop 32 is attached to a manipulation wire 34 which permits the loop 32 to be advanced over the forward end of the grasper to encircle and close the left atrial appendage, as will be described in more detail below. The grasping tool 30 may be manipulated using a thumb guide 40, while the capture loop 32 may be manipulated using a second thumb guide 42, both of which are located on the handle 18.

The lumens 20, 22, and 24, terminate in exit ports 50, 52, and 54, best seen in FIG. 4A. The exit ports are located proximally of the distal end 14 of the shaft 12. The shaft is generally thinned in the region between the exit ports and the distal tip, facilitating the introduction of the distal tip into the atrioventricular groove, as described in more detail below. The exit ports are located a sufficient distance behind the distal tip of the shaft so that they will be generally located adjacent to the free end of the left atrial appendage when the tip is located in the atrioventricular groove.

Figure 5:
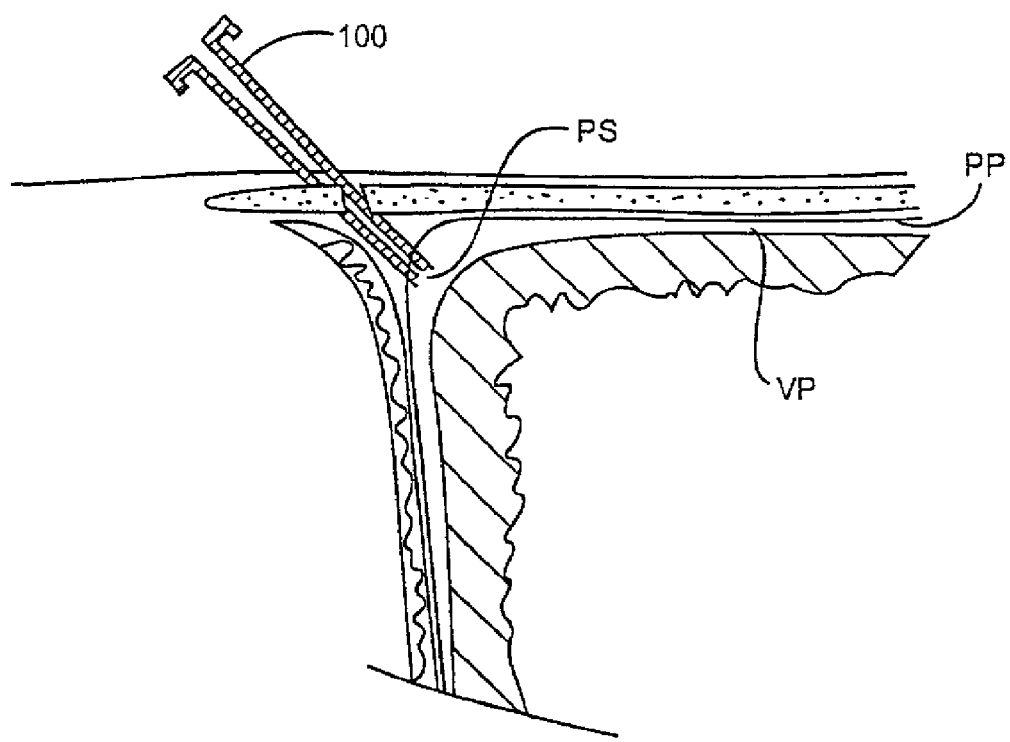
FIG. 5 illustrates an access sheath placed percutaneously into a pericardial space using a sub-xiphoid approach beneath the rib cage as is preferred in the methods of the present invention.
Figure 6A:
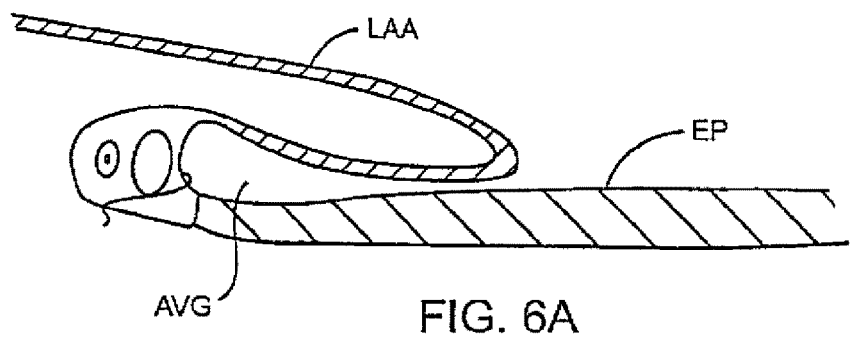
FIGS. 6A-6G illustrate use of the exemplary tool of FIG. 3 in performing the closure of a left atrial appendage according to the methods of the present invention.
Figure 6B:
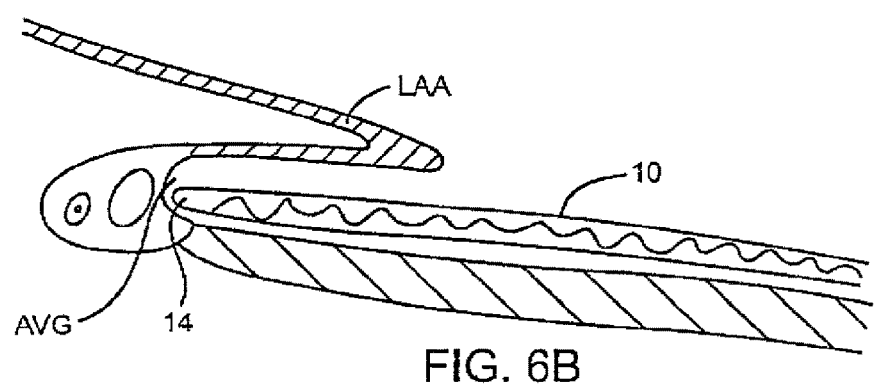
Figure 6C:
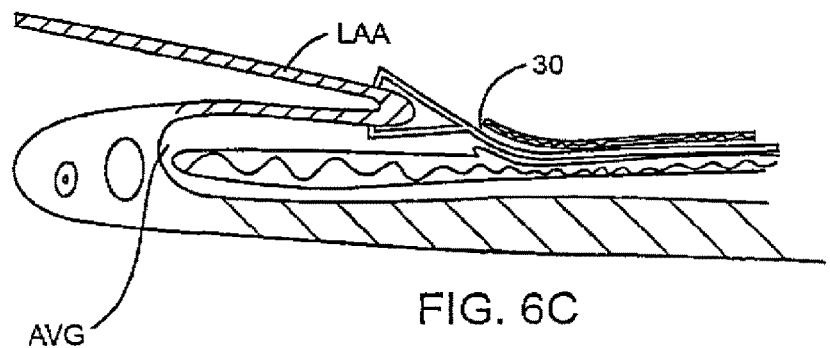
Figure 6D:
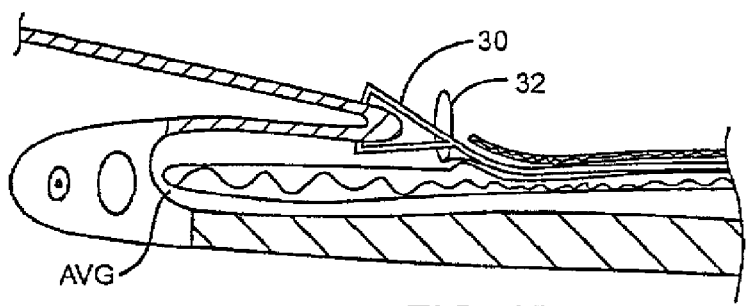
Figure 6E:
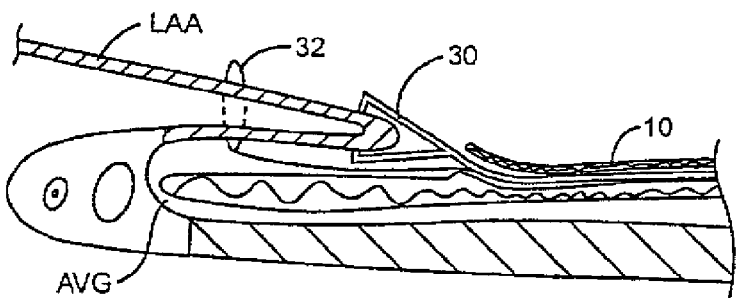
Figure 6F:
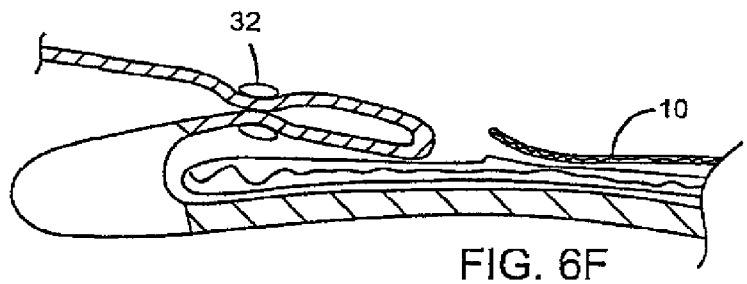
Figure 6G:
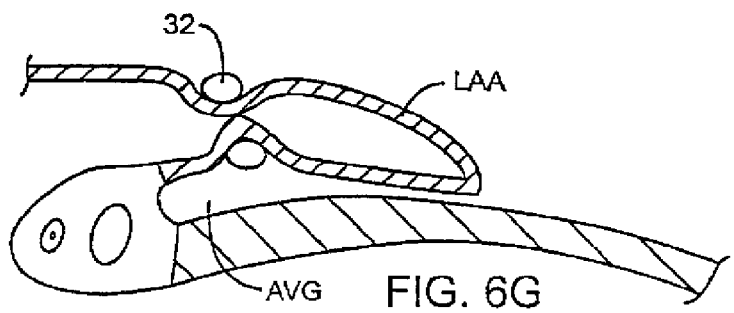

The methods of the present invention may be performed in an ambulatory surgical setting. Typically, a sedated patient is taken to a facility having fluoroscopic imaging capabilities. The area overlying the xiphoid and adjacent costal cartilage, is prepared and draped using standard techniques. A local anesthetic is then administered and a skin incision, usually about 2 cm in length made, at the area shown in FIG. 2. The percutaneous penetration passes beneath the costal cartilage, and a sheath 100 (FIG. 5) is introduced into the pericardial space PS. The pericardial space PS is then irrigated with saline, preferably with a saline-lidocaine solution to provide additional anesthesia and reduce the risk of irritating the heart. The closure device 10 is then introduced through the sheath 100 into the pericardial space and advanced over the epicardium to the atrioventricular groove AVG (as shown in FIG. 6A and FIG. 6B). The grasping tool 30 is then advanced distally from the tool 10 so that it can grasp the free end of the left atrial appendage LAA, as shown in FIG. 6C. A slight tension can be applied on the left atrial appendage LAA as the capture loop 32 is advanced over the grasper 30 (FIG. 6D), and on to the left atrial appendage LAA, as shown in FIG. 6E. The loop may then be cinched, as shown in FIG. 6F, and the tool 10 withdrawn leaving the closure loop in place, as shown in FIG. 6G. The interior of the left atrial appendage LAA is thus isolated from the interior of the left atrium so that thrombus and other emboli cannot be released into blood circulation.

Figure 6H:
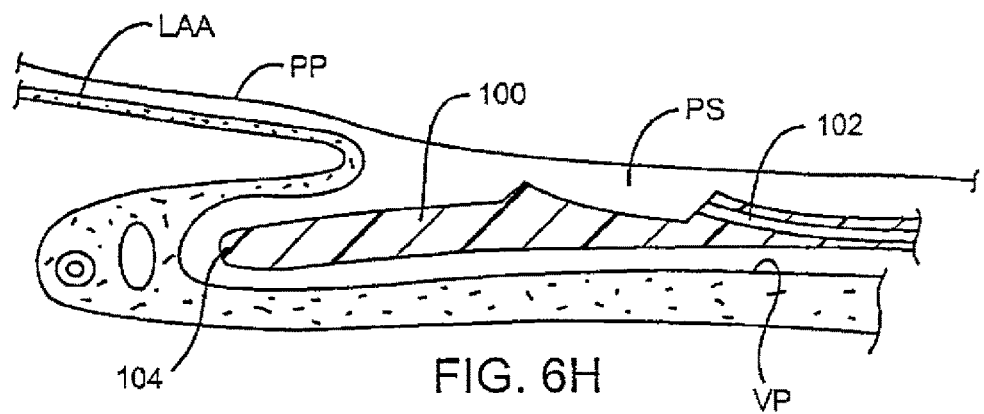
FIGS. 6H-6J illustrate a modified closure device for introduction of a balloon expander.
Figure 6I:
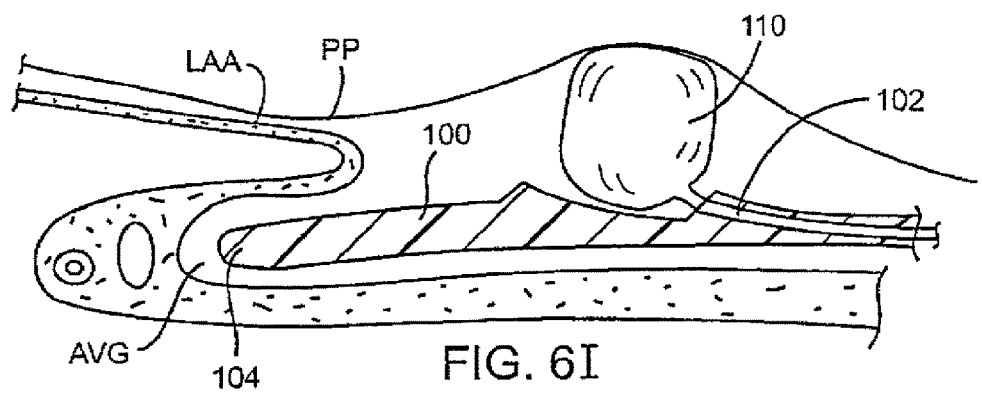
Figure 6J:
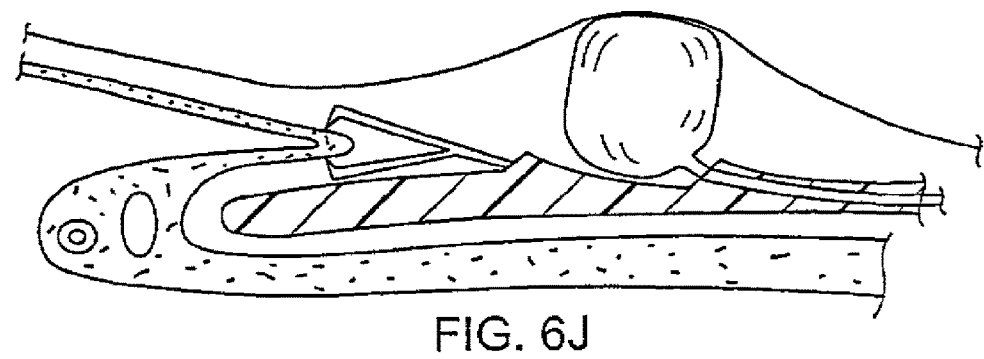
Figure 6K:
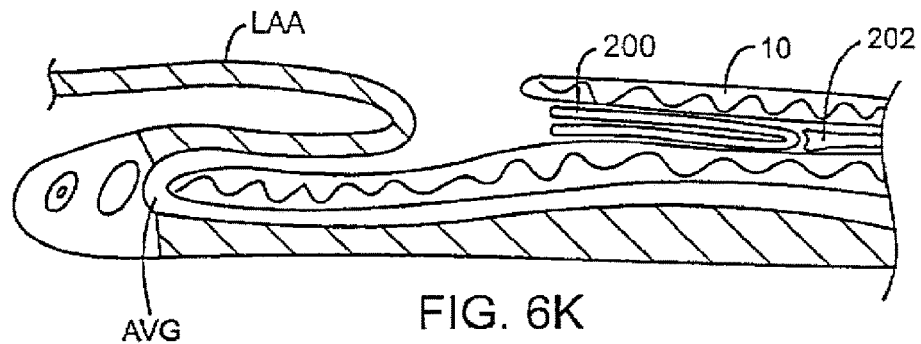
FIGS. 6K-6N illustrate an alternative protocol for use of the exemplary tool of FIG. 3 in performing the closure of a left atrial appendage according to the methods of the present invention.

Optionally, a portion of the parietal pericardium may be further separated from the epicardial surface and the left atrial appendage prior to closing the appendage. Increasing the distance between the parietal and visceral pericardium, i.e., the pericardial space, creates a working and viewing space that facilitates subsequent manipulation and closure of the atrial appendage. As shown in FIGS. 6H-6J, a modified closure device 100 having an additional lumen 102 is introduced so that its distal end 104 enters the atrioventricular groove AVG, as described previously. A balloon expander 110 may then be introduced through the lumen 102, and the balloon expanded to raise the pericardium, as shown in FIG. 6I. The grasper 30 (or other closure instrument) may then be introduced through other lumens, as previously described. The working space created by the balloon greatly simplifies manipulation and positioning of the graspers 30 so that they can be used to capture the atrial appendage and close it as described previously. Further separating the parietal and visceral pericardia to create the working space is a particular advantage when a viewing scope is introduced to the working area to facilitate manipulation of the grasper 30 and any other tools which may be used.

Figure 6L:
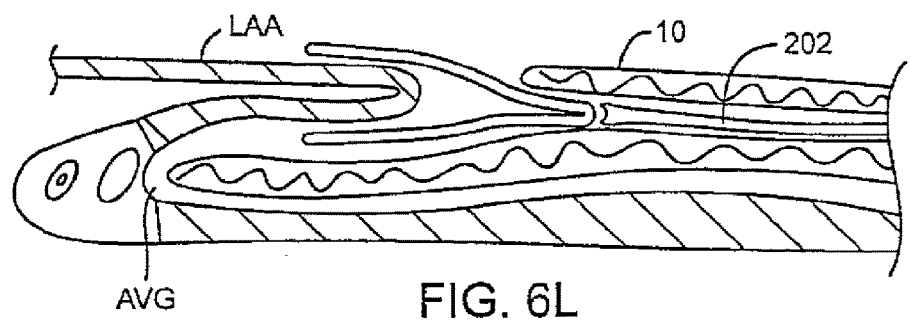
Figure 6M:
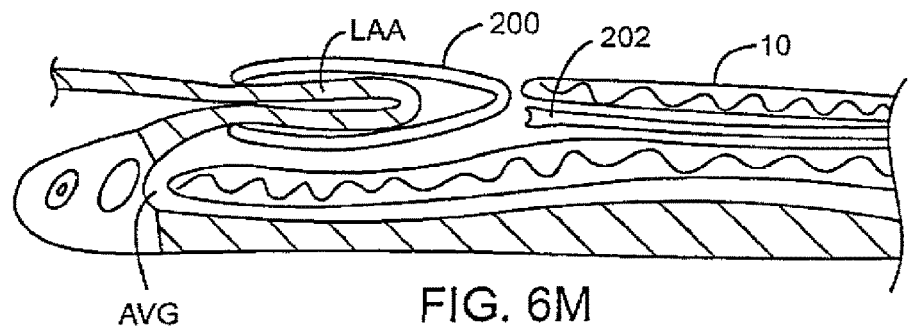
Figure 6N:
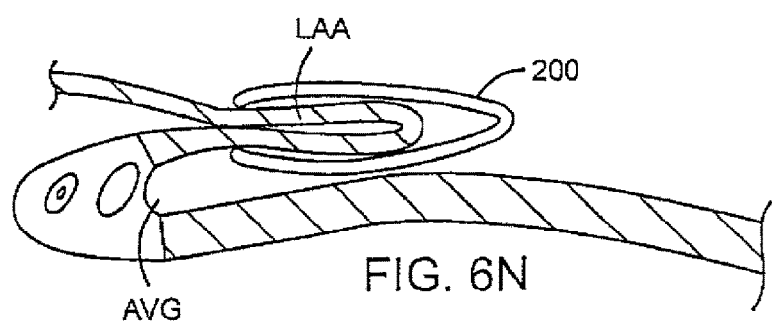
Figure 6O:
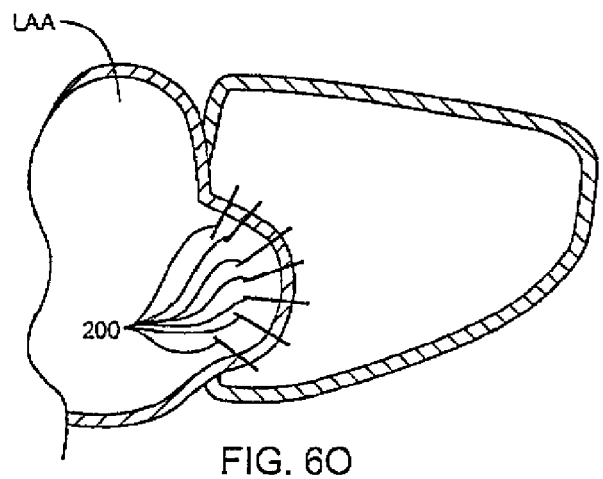
FIGS. 6O and 6P illustrate alternative clip placement patterns for closing the left atrial appendage according to the methods of the present invention.
Figure 6P:
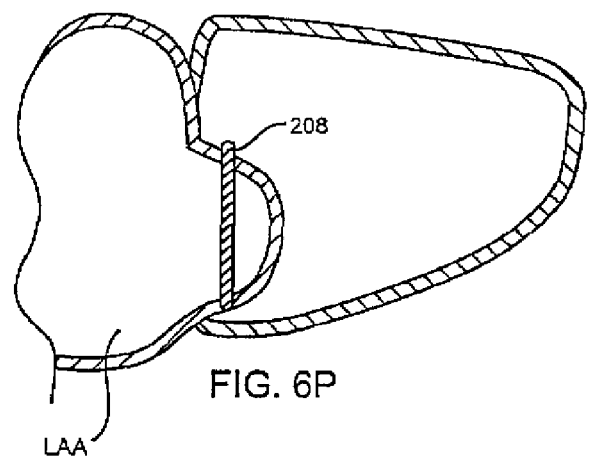

Referring now to FIGS. 6K-6N, the closure tool 10 is illustrated in a method for introducing a clip 200 in accordance with the principles of the present invention. The closure tool 10 is introduced to the left atrial appendage LAA as described in above in connection with FIGS. 6A and 6B. Once in place, the clip 200 may be introduced through any of the available lumens in the device, typically using a pusher 202. The clip 200 will be configured so that it opens as it emerges from the closure tool 10 and can be advanced over the free distal end of the left atrial appendage LAA, as shown in FIG. 6L. The clip 200 may then be closed over the appendage, as shown in FIG. 6N. The clip 200 may be self-closing or may require a mechanical or heat-actuated closure mechanism. Once in place, as shown in FIG. 6N, the closure tool 10 can be removed. Frequently, it will be desirable to introduce multiple clips 200, as shown in FIG. 6O. Alternatively, a larger clip 208 can be introduced transversely over the left atrial appendage LAA, as shown in FIG. 6P.

Referring now to FIGS. 7A-7C, an exemplary clip 300 for use in the methods of the present invention will be described. The clip 300 has a generally U-shaped profile, as best seen in FIG. 7A, optionally having a serpentine or zig-zag profile on at least one of the legs of the clip. As illustrated, a series of peaks and valleys 302 is provided on an "upper" leg of the clip. The clip 300 further includes a hinge region 304 which has a narrowed width to facilitate introduction through a introducer catheter 400, as shown in FIG. 8. Introducer catheter 400 has a I-shaped lumen 402 which receives the clip 300 so that the upper leg and lower leg of the clip are held in an open configuration in upper and lower tracks of the lumen, as described below in connection with FIGS. 9A-9C. Optionally, the catheter 400 may include a radiopaque marker 404 to permit orientation under fluoroscopic imaging (so the position can confirm that the clip is in the proper vertical orientation when being placed). A pusher 408 is provided having a I-shaped distal end 410 which is received in the I-shaped lumen 402 in order to advance and eject the clip from the catheter.

Figure 9A:
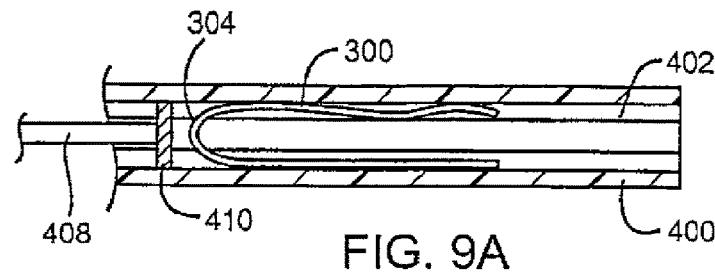
FIGS. 9A-9C are cross-sectional views of the insertion tool of FIG. 8 used in placing the clip of FIG. 7A-7C over a left atrial appendage according to the methods of the present invention.
Figure 9B:
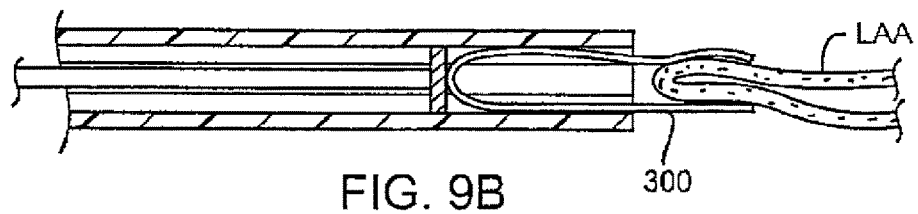
Figure 9C:
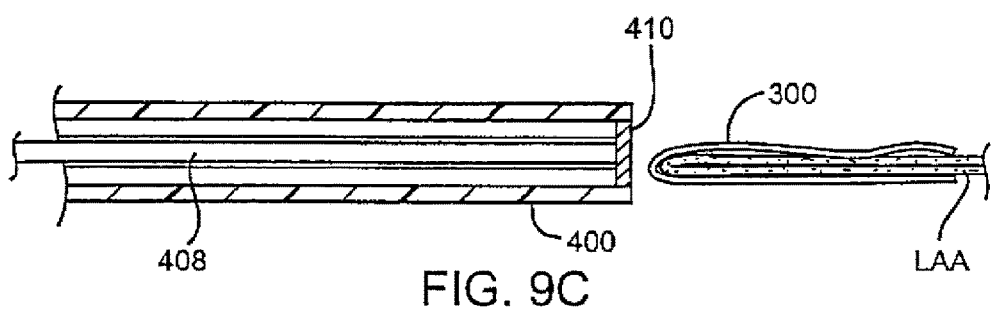

Referring now to FIGS. 9A-9C, the clip 300 is held in the lumen 402 of catheter 400 with the legs of the clip held open. A pusher 408 can be advanced so that end 410 engages the hinge region 304 of the clip, allowing it to be advanced out of the distal end of the catheter, as shown in FIG. 9B. As the clip 300 emerges, it remains in an open configuration so that it can be advanced over a free distal end of the left atrial appendage LAA, as shown in FIG. 9B. Once the clip 300 is fully advanced and released from the catheter 400, as shown in FIG. 9C, the clip will close over the left atrial appendage LAA to hold the appendage closed in accordance with the principles of the present invention.

Figure 10:
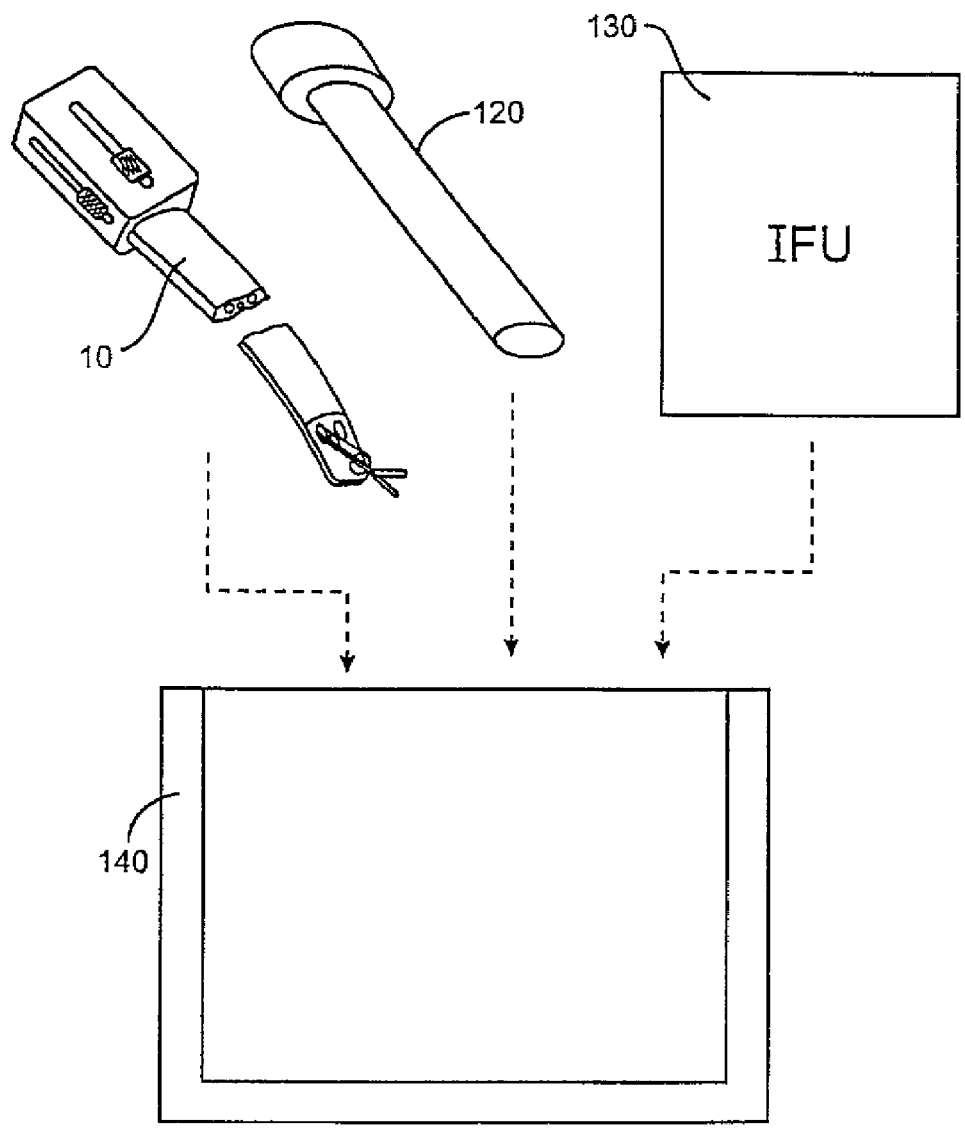
FIG. 10 illustrates an exemplary kit including a closure device and optional components acconding to the present invention.

Referring now to FIG. 10, kits according to the present invention comprise a closure tool, such as closure tool 10 described above. Optionally, the kits may comprise an access sheath 120 and will include instructions for use IFU setting forth any of the methods described above. Usually, all components of the kit will be packaged together in an enclosure 140, such as a pouch, tray, box, tube, or other conventional surgical package capable of maintaining the components in a sterile condition. It will be appreciated that any kit containing instructions for use setting forth the methods of the present invention will be part of the present invention. Whether or not the kits include a closure device which is similar to FIG. 10 is not necessary.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for closing a left atrial appendage of a patient's heart, said method comprising:
    advancing a closure tool adjacent to the left atrial appendage using a sub-xiphoid approach; and
    closing the left atrial appendage using the closure tool.

2. The method of claim 1, wherein closing comprises looping, suturing, stapling, clipping, riveting, clamping, or fusing the left atrial appendage at a neck region thereof.

3. The method of claim 2, wherein closing further comprises engaging the left atrial appendage prior to closing the neck region thereof.

4. The method of claim 1, wherein the method is performed while the patient's heart is beating.

5. The method of claim 4, wherein the method is performed while both lungs of the patient remain inflated.

6. The method of claim 5, wherein the method is performed while the patient is under a local anesthetic.

7. The method of claim 1, further comprising separating the parietal pericardium from the visceral pericardium near the left atrial appendage prior to closing the left atrial appendage to create a space over the left atrial appendage.

8. The method of claim 7, further comprising viewing the left atrial appendage through the space.

9. The method of claim 1, wherein advancing further comprises advancing a distal end of the closure tool through a sheath, into the pericardial space, and over an epicardial surface.

10. The method of claim 1, wherein the closure tool comprises a shaft and a closure loop, and wherein closing the left atrial appendage comprises advancing the closure loop over the left atrial appendage and cinching the loop.

11. The method of claim 1, wherein the closure tool comprises a shaft and a clip, and wherein closing the left atrial appendage comprises advancing the clip over a distal end of the left atrial appendage and closing the clip.

12. A method for closing a left atrial appendage of a patient's heart, said method comprising:
 advancing a loop adjacent to the left atrial appendage using a sub-xiphoid approach; and
 closing the left atrial appendage using the loop.

13. The method of claim 12, wherein closing comprises suturing the left atrial appendage at a neck region thereof.

14. The method of claim 13, wherein closing further comprises engaging the left atrial appendage prior to closing the neck region thereof.

15. The method of claim 12, wherein the method is performed while the patient's heart is beating.

16. The method of claim 15, wherein the method is performed while both lungs of the patient remain inflated.

17. The method of claim 16, wherein the method is performed while the patient is under a local anesthetic.

18. The method of claim 12, further comprising separating the parietal pericardium from the visceral pericardium near the left atrial appendage prior to closing the left atrial appendage to create a space over the left atrial appendage.

19. The method of claim 18, further comprising viewing the left atrial appendage through the space.

20. The method of claim 12, wherein advancing further comprises advancing the loop through a sheath, into the pericardial space, and over an epicardial surface.

* * * * *